(12) United States Patent
Lunstad et al.

(10) Patent No.: US 9,802,975 B2
(45) Date of Patent: Oct. 31, 2017

(54) PROTECTING GROUPS FOR "Z NUCLEOTIDE" AND METHODS THEREOF

(71) Applicant: Agilent Technologies, Inc., Loveland, CA (US)

(72) Inventors: Benjamin D. Lunstad, Santa Clara, CA (US); Douglas J. Dellinger, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 126 days.

(21) Appl. No.: 14/724,613

(22) Filed: May 28, 2015

(65) Prior Publication Data

US 2015/0353594 A1 Dec. 10, 2015

Related U.S. Application Data

(60) Provisional application No. 62/010,402, filed on Jun. 10, 2014.

(51) Int. Cl.
| | |
|---|---|
| *C07H 5/06* | (2006.01) |
| *C07H 7/06* | (2006.01) |
| *C07H 23/00* | (2006.01) |
| *C07H 21/00* | (2006.01) |
| *C07D 211/00* | (2006.01) |

(52) U.S. Cl.
CPC .......... *C07H 23/00* (2013.01); *C07D 211/00* (2013.01); *C07H 7/06* (2013.01); *C07H 21/00* (2013.01); *Y02P 20/55* (2015.11)

(58) Field of Classification Search
CPC .................. C07H 7/06; C07H 23/00
See application file for complete search history.

(56) References Cited

U.S. PATENT DOCUMENTS

| 6,800,743 | B2 | 10/2004 | Lin et al. | |
|---|---|---|---|---|
| 7,105,499 | B2* | 9/2006 | Carroll | A61K 31/7076 514/42 |
| 7,598,373 | B2* | 10/2009 | Storer | C07H 1/00 536/1.11 |
| 8,202,983 | B2 | 6/2012 | Dellinger et al. | |
| 8,389,703 | B1 | 3/2013 | Benner et al. | |
| 8,586,303 | B1 | 11/2013 | Benner et al. | |
| 9,067,961 | B2 | 6/2015 | Dellinger et al. | |
| 2004/0110717 | A1 | 6/2004 | Carroll et al. | |
| 2005/0020825 | A1 | 1/2005 | Storer et al. | |

FOREIGN PATENT DOCUMENTS

| WO | WO2009154733 | 12/2009 |
|---|---|---|
| WO | WO 2014/022739 | 2/2014 |

OTHER PUBLICATIONS

Chen, et al. "Recognition of an expanded genetic alphabet by type-II restriction endonucleases and their application to analyze polymerase fidelity", 2011, Nucleic Acids Research, 39(9) 3949-3961.
Nutter, et al. "Expanding the Genetic Alphabet: Non-Epimerizing Nucleoside with the pyDDA Hydrogen-Bonding Pattern", 2003, J. Org. Chem., 68(25) 9839-9842.
Kim, et al. "Ribonucleosides for an Artificially Expanded Genetic Information System", 2014, J. Org. Chem. 79 (7) 3194-3199.
Kim, et al. "Synthesis and Properties of 5-Cyano-Substituted Nucleoside Analog with a Donor—Donor—Acceptor Hydrogen-Bonding Pattern", 2012, J. Org. Chem. 77 (7) 3664-3669.
Yang, et al. "Amplification, Mutation, and Sequencing of a Six-Letter Synthetic Genetic System", 2011, J. Am. Chem. Soc. 133 (38) 15105-15112.
Yang, et al. "Expanded Genetic Alphabets in the Polymerase Chain Reaction", 2010, Angewandte Chemie, International Edition 49(1) 177-180, S177/1-S177/16.
Yang, et al. "Enzymatic incorporation of a third nucleobase pair", 2007, Nucleic Acids Research 35(13) 4238-4249.
Yang, et al. 8. Yang, et al. "Artificially expanded genetic information system: a new base pair with an alternative hydrogen bonding pattern", 2006, Nucleic Acids Research 34(21) 6095-6101.

* cited by examiner

*Primary Examiner* — Lawrence E Crane

(57) ABSTRACT

The present disclosure provides nucleoside compounds and oligonucleotides including an unnatural 6-amino-2-pyridone heterocyclic base where the 6-amino and 2-positions are protected. The 2-position of the heterocyclic base can be protected with an acyl-oxy-methyl protecting group. In some embodiments, the protected heterocyclic base has the following structure where AcOM is an acetyl-oxy-methyl group and R is a ribose or deoxyribose sugar:

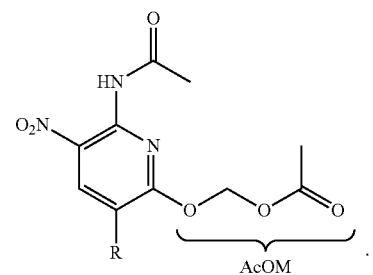

Methods for synthesizing an oligonucleotide are provided in which the subject compounds find use. The method can include protecting an unnatural (e.g., Z) nucleotide with an acetyl-oxy-methyl group; incorporating the protected unnatural nucleotide into a nucleotide sequence on a solid support; and removing the acetyl-oxy-methyl group from the unnatural nucleotide incorporated into the nucleotide sequence. The compounds and methods find use in the synthesis of long oligonucleotides including Z nucleotides.

20 Claims, 7 Drawing Sheets

PROTECTING GROUPS FOR "Z NUCLEOTIDE" AND METHODS THEREOF

CROSS REFERENCE TO RELATED APPLICATION

This application claims the benefit of U.S. provisional application Ser. No. 62/010,402, filed on Jun. 10, 2014, which application is hereby incorporated by reference herein in its entirety.

GOVERNMENT RIGHTS

This invention was made with government support under N66001-12-C-4211 awarded by DARPA. The government has certain rights in the invention.

FIELD OF THE INVENTION

The invention generally relates to synthesis of nucleic acids. More particularly, the invention relates to novel protecting groups and related compounds useful in the synthesis of DNAs and RNAs with one or more "Z nucleotides" incorporated into their sequences, and methods thereof.

BACKGROUND OF THE INVENTION

Nucleic acids are biological molecules essential for all known forms of life. Nucleic acids, which include DNA (deoxyribonucleic acid) and RNA (ribonucleic acid), are made from nucleotides. Nucleic acids function in encoding, transmitting and expressing genetic information. Studies of nucleic acids are a critical part of modern biological and medical research, which form a foundation for genomics as well as the biotechnology and pharmaceutical industries.

Feeling the constraints set by the very limited number of naturally occurring nucleotides in standard nucleic acids, scientists have for years attempted to introduce unnatural base pair systems in an effort to expand the genetic code. One such unnatural base pair is the so-called "Z-P" system developed by Steven Benner and collaborators in which the synthetic nucleotide Z can pair with the synthetic nucleotide P via 3 hydrogen bonds. (Kim, et al. 2014 *J. Org. Chem.* 79 (7) 3194-3199; Yang, et al. 2013 *Anal. Chem.* 85 (9) 4705-4712, Kim, et al. 2012 *J. Org. Chem.* 77 (7) 3664-3669; Yang, et al. 2011 *J. Am. Chem. Soc.* 133 (38) 15105-15112; Chen, et al. 2011 *Nucleic Acids Research* 39(9) 3949-3961; Yang, et al. 2010 *Angewandte Chemie*, International Edition 49(1) 177-180, S177/1-S177/16; Yang, et al. 2007 *Nucleic Acids Research* 35(13) 4238-4249; Yang, et al. 2006 *Nucleic Acids Research* 34(21) 6095-6101; Hutter, et al. 2003 *J. Org. Chem.* 68(25) 9839-9842; WO 2009/154733 A2; U.S. Pat. No. 8,389,703 B1; U.S. Pat. No. 8,586,303 B1.)

Among the important requirements for a proposed unnatural base pair to serve as components of the expanded genetic code, it must allow for easy, clean incorporation of the unnatural nucleotides into DNA and RNA molecules by conventional chemical DNA and RNA synthesis. Oligonucleotide synthesis of desired length and sequence with defined chemistry is a fundamental criterion in both laboratory research and applications in molecular biology and medicine.

During oligonucleotide synthesis, in order to prevent undesired side reactions, select functional groups present in nucleosides have to be rendered unreactive or "protected" by attaching protecting groups. The protecting groups are removed to yield the desired oligonucleotides at the completion of a particular synthetic step or after the assembly of an oligonucleotide.

One of the few reported protecting groups used for the Z nucleotide base when making synthetic DNA (or RNA) incorporating Z nucleotide is a para-nitro phenylethyl (NPE) protecting group (U.S. Pat. No. 8,389,703 B2.) However, experiments to make RNA containing Z nucleotides protected with NPE have shown that this protecting group is far from ideal. In fact, significant damage to oligonucleotide product occurs during deprotection along with undesired modification of the Z nucleotide itself. As a result, currently there is no viable protection strategy for efficient synthesis of oligonucleotides incorporating Z nucleotide, which severely restricts the utility of the Z-P unnatural base pair.

Thus, there is an urgent need to develop novel protecting groups and methodologies to enable easy chemical incorporation of unnatural nucleotides, in particular Z nucleotides, into synthesized long oligonucleotides.

SUMMARY OF THE INVENTION

The present disclosure provides a unique methodology and protecting groups that enable synthesis of oligonucleotides having Z nucleotide in an easy, clean and site-specific fashion with high yield. In particular, the method causes little to no damage to oligonucleotide product and does not modify the Z nucleotide itself. The invention provides a viable protection strategy for efficient synthesis of long oligonucleotides with Z nucleotide incorporated therein.

In one aspect, the invention generally relates to a compound having the structural formula (I):

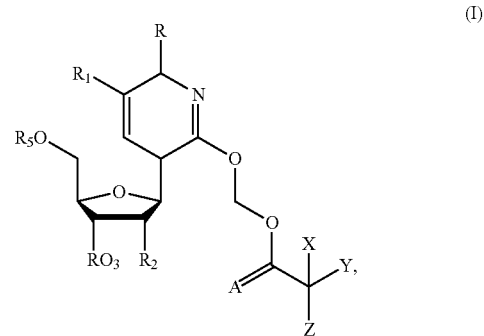

(I)

wherein
$R_1$ is $NO_2$, CN, F, or $C_1$-$C_4$ perfluoroalkyl;
A is O or S;
$R_2$ is a H, O-methyl, fluorine, or $OR_{2'}$, wherein $R_{2'}$ is a first protecting group;
$R_3$ is a second protecting group;
$R_5$ is a third protecting group;
R is a protected amino group of the formula N=C(R)NR$_2$ or N(R)COR or N(COR)$_2$

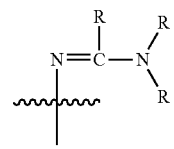

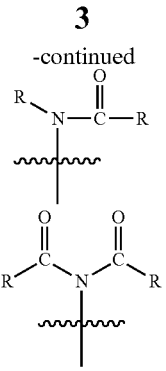

wherein each R is independently selected from H, linear-, branched-, saturated- or unsaturated-alkyl, aryl, alkaryl or aralkyl; and wherein R is a protected amino group of the formula N=C(R)NR$_2$, NR$_2$ may be joined to form a 5-8 membered ring wherein said ring can contain a heteroatom selected from O or S; and each of X, Y and Z is independently H, halogen, or a C$_1$-C$_3$ alkyl, wherein two or more of X, Y and Z may together form a 5-8 membered saturated, un-saturated or aryl ring.

In another aspect, the invention generally relates to an oligonucleotide, wherein at least one of the nucleotides has the structural formula of:

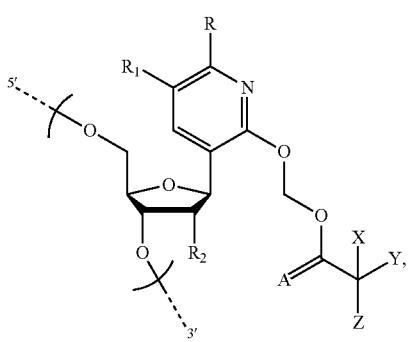

(V)

wherein
R$_1$ is NO$_2$, CN, F, or C$_1$-C$_4$ perfluoroalkyl,
A is O or S;

R$_2$ is 1,1-dioxo-thiomorpholine-4-carbothioate (TC), tert-butyldimethylsilyl (TBDMS), tri-iso-propylsilyloxymethyl (TOM), bis(2-acetoxyethoxy)methyl (ACE), pivaloyloxymethyl (PivOM), 1-(2-cyanoethoxy)ethyl (CEE), 2-cyanoethoxymethyl (CEM), —CO—R", —CH$_2$—CH=CH$_2$, —CH$_2$—O—CH$_2$-phenyl-NO$_2$, —CH$_2$—O—CH$_2$—CH$_2$—SO$_2$-aryl, CH$_2$—S—S—R$_1$, —Si(R")$_3$; wherein R" is independently selected from straight-, branched-, saturated or unsaturated-alkyl, aryl, alkaryl, and aralkyl;

R is a protected amino group of the formula N=C(R') NR'$_2$ or N(R')COR' or N(COR')$_2$ wherein each R' is independently selected from H, linear-, branched-, saturated- or unsaturated-alkyl, aryl, alkaryl and aralkyl; or wherein R is a protected amino group of the formula N=CR'NR'$_2$, wherein NR'$_2$ is joined to form a 5-8 membered ring wherein said ring can contain a heteroatom selected from O or S; and each of X, Y and Z is independently H, halogen, or a C$_1$-C$_3$ alkyl, wherein two or more of X, Y and Z may together form a 5-8 membered saturated, un-saturated or aryl ring.

In yet another aspect, the invention generally relates to a method for synthesizing an oligonucleotide using a compound disclosed herein. The synthesized oligonucleotide may be a DNA, an RNA or a mixed sequence of DNA and RNA including one or more unnatural nucleotides.

In yet another aspect, the invention generally relates to a method for synthesizing an oligonucleotide. The method includes: protecting an unnatural nucleotide with an acetyl-oxy-methyl group, incorporating the protected unnatural nucleotide to an oligonucleotide sequence; and removing the acetyl-oxy-methyl group from the unnatural nucleotide incorporated in the oligonucleotide sequence. The protected unnatural nucleotide incorporated in the oligonucleotide sequence has the structural formula (V),

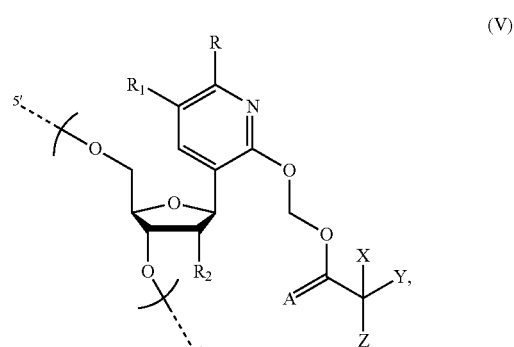

(V)

wherein
R$_1$ is R$_1$ is NO$_2$, CN, F, or C$_1$-C$_4$ perfluoroalkyl,
A is O or S, R$_2$ is 1,1-dioxo-thiomorpholine-4-carbothioate (TC), tert-butyldimethylsilyl (TBDMS), tri-iso-propylsilyloxymethyl (TOM), bis(2-acetoxyethoxy)methyl (ACE), pivaloyloxymethyl (PivOM), 1-(2-cyanoethoxy)ethyl (CEE), 2-cyanoethoxymethyl (CEM), —CO—R", —CH$_2$—CH=CH$_2$, —CH$_2$—O—CH$_2$-phenyl-NO$_2$, —CH$_2$—O—CH$_2$—CH$_2$—SO$_2$-aryl, CH$_2$—S—S—R$_1$, or —Si(R")$_3$; wherein R" is independently selected from straight-, branched-, saturated or unsaturated-alkyl, aryl, alkaryl, or aralkyl;

R is a protected amino group of the formula N=C(R') NR'$_2$ or N(R')COR' or N(COR)$_2$ wherein each R' is independently selected from H, linear-, branched-, saturated- or unsaturated-alkyl, aryl, alkaryl or aralkyl; or wherein R is a protected amino group of the formula N=CRNR$_2$, wherein NR$_2$ is joined to form a 5-8 membered ring wherein said ring can contain a heteroatom selected from O or S; and each of X, Y and Z is independently H, halogen, or a C$_1$-C$_3$ alkyl, wherein two or more of X, Y and Z may together form a 5-8 membered saturated, un-saturated or aryl ring.

In yet another aspect, the invention generally relates to a method for synthesizing an oligonucleotide. The method includes: protecting a nucleotide with an acetyl-oxy-methyl group,

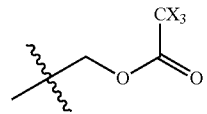

wherein each X is independently H or a halogen; chemically incorporating the protected nucleotide to an oligonucleotide sequence; and removing the acetyl-oxy-methyl group from the nucleotide incorporated in the nucleotide sequence.

DEFINITIONS

Figure 1:
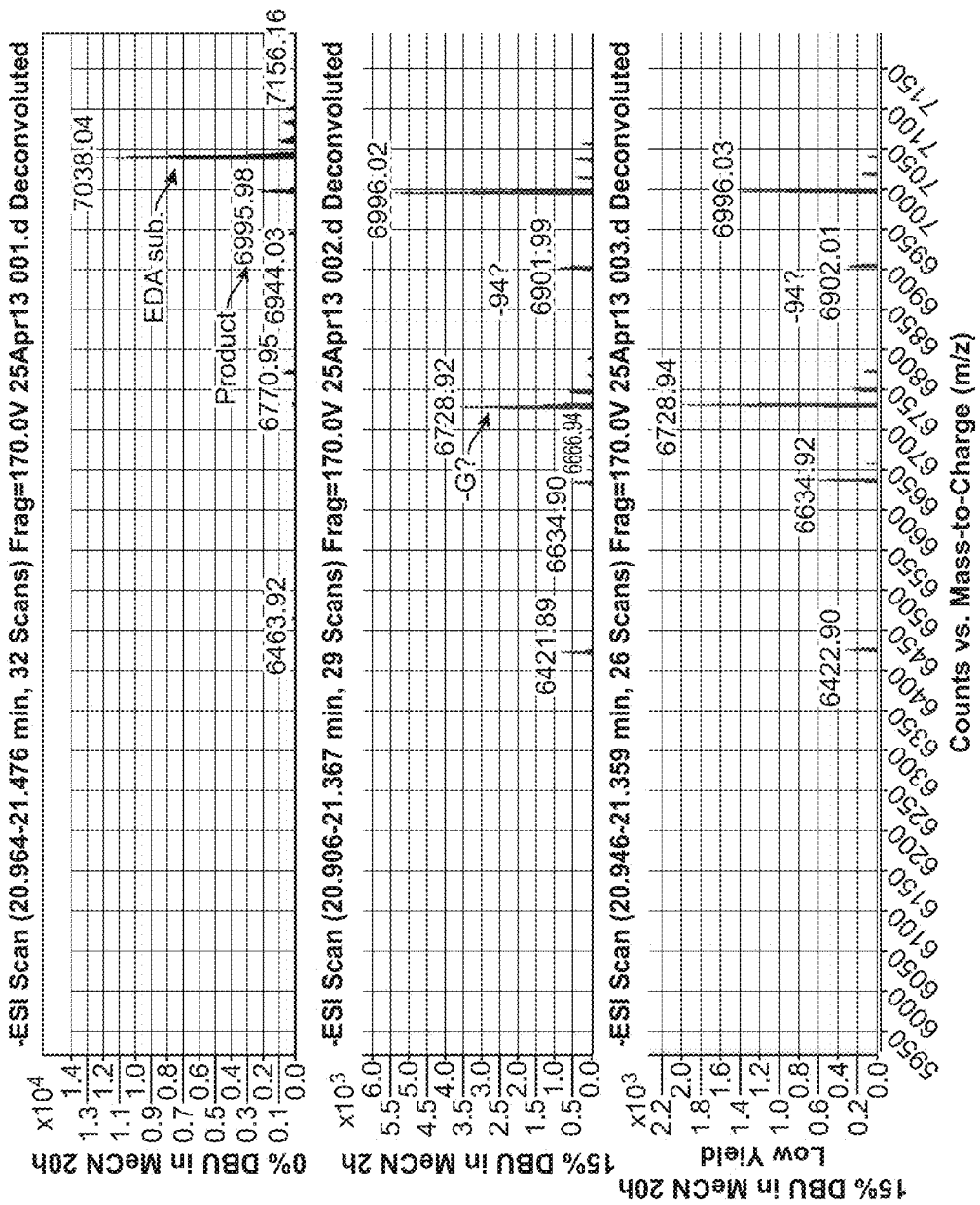
FIG. 1: Electrospray mass spectrometry plots (ESI scans) showing a 21-mer RNA synthesis results using para-nitrophenylethyl (NPE) as rZ protecting group and 1M (15%) DBU followed by EDA for deprotection and cleavage from the support. Top panel: ESI scan of RNA synthesis using standard 5 hour EDA deprotection method (no DBU). Middle and lower panels: ESI scans of RNA synthesis using a two-step deprotection protocol using 1M (15%) DBU followed by EDA to complete deprotection and cleavage from support. Middle panel shows a 2 hour process while the lower panel shows a 20 hour process. Desired product peak is indicated as "product" as well as EDA substituted product (labeled "EDA sub.") and certain degradation products (−G and −94). (−G=expected RNA species lacking a G nucleotide; −94=expected RNA product having a molecular mass that is 94 daltons less than desired RNA product).

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios, inter alia, are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

Terms and symbols of nucleic acid chemistry, biochemistry, genetics, and molecular biology used herein follow those of standard treatises and texts in the field, e.g. Kornberg and Baker, DNA Replication, Second Edition (W.H.

Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, 2nd Edition (Cold Spring Harbor Laboratory, 1989); and the like. Still, certain terms are defined below for the sake of clarity and ease of reference.

It will be appreciated that the compounds, as described herein, may be substituted with any number of substituents or functional moieties.

The term "alkyl", as used herein, refers to a saturated straight chain, branched or cyclic hydrocarbon group (e.g., having 1 to 24, typically 1 to 12) carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, or 2,3-dimethylbutyl. Alkyls include "cycloalkyls", which refer to cyclic alkyl groups such as cyclopropyl, cyclobutyl, cyclopentyl, cyclohexyl, cycloheptyl or cyclooctyl.

The term "alkoxy" means an alkyl group linked to oxygen and may be represented by the formula: R—O—, wherein R represents the alkyl group. An example is the methoxy group $CH_3O—$.

The term "aryl" refers to 5-, 6-, and 7-membered single- or multi-ring aromatic groups that may include from zero to four heteroatoms, for example, benzene, pyrrole, furan, thiophene, imidazole, oxazole, thiazole, triazole, pyrazole, pyridine, pyrazine, pyridazine or pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). An example of a fused ring aryl group is naphthalene. A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, or —CN, and the like.

The terms "nucleotide", as used herein, refer to a sub-unit of a nucleic acid (whether DNA or RNA or analogue thereof), which includes a phosphate group, a sugar group and a heterocyclic base, as well as analogs of such sub-units. Other groups (e.g., protecting groups) can be attached to any component(s) of a nucleotide.

The term "alkylaryl", as used herein, refers to an aryl group with an alkyl substituent. The term "aralkyl" or "arylalkyl", as used herein, refers to an alkyl group with an aryl substituent.

The terms "nucleoside", as used herein, refer a nucleic acid subunit including a sugar group and a heterocyclic base, as well as analogs of such sub-units. Other groups (e.g., protecting groups) can be attached to any component(s) of a nucleoside.

The terms "nucleotide" and "nucleoside" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, alkylated purines or pyrimidines, acylated purines or pyrimidines, halogenated purines or pyrimidines, deazapurines, alkylated riboses or other heterocycles. Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, and substituted phenoxyacetyl, dimethylformamidine, dibutylformamidine, pyrrolodinoamidine, morpholinoamidine, and other amidine derivatives, or N,N-diphenyl carbamate, and the like. The purine or pyrimidine base may also be an analog of the foregoing; suitable analogs will be known to those skilled in the art and are described in the pertinent texts and literature. Common analogs include, but are not limited to, 7-deazaadenine, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups including locked nucleic acids (known as LNA) and unlocked nucleic acids (UNA), 2'-fluoro, 2'-O-alkyl, or 2'-O-ethoxymethoxy, or are functionalized as ethers or amines, and the like.

The terms "Z nucleotide" and "P nucleotide", as used herein, refer to two unnatural nucleotides that can form a base pair, as shown below.

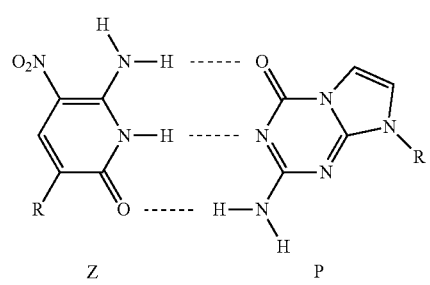

The term "analogues", as used herein, refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking groups.

The term "oligonucleotide", as used herein, refers to a single stranded multimer of nucleotides of from about 2 to about 500 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers or both and may optionally include nucleotide analogues. Oligonucleotides may be, inter alia, 10 to 20, 21 to 30, 31 to 40, 41 to 50, 51-60, 61 to 70, 71 to 80, 80 to 100, 100 to 150, 150 to 500 or greater than 500 nucleotides in length, for example.

The term "nucleic acid", as used herein, refers to a polymer of any length (e.g., inter alia, greater than about 2 bases, greater than about 10 bases, greater than about 100 bases, greater than about 500 bases, greater than about 1,000 bases, up to about 10,000 or more bases) composed of nucleotides (e.g., deoxyribonucleotides, ribonucleotides, or both, and may include one or more unnatural nucleotides) which may be produced enzymatically or synthetically, and which can hybridize in a sequence specific manner to a complementary nucleotide in a manner analogous to that of two naturally occurring nucleotides (e.g., can participate in Watson-Crick base pairing interactions). Naturally-occurring nucleotides include guanosine and 2'-deoxyguanosine, cytidine and 2'-deoxycytidine, adenosine and 2'-deoxyadenosine, thymidine and uridine (G, dG, C, dC, A, dA and T, U respectively). Unnatural nucleotides include Z and P nucleotides.

A nucleic acid may exist in a single-stranded or a double-stranded form. A double-stranded nucleic acid has two complementary strands of nucleic acid (which may be referred to herein as the "first" and "second" strands or some other arbitrary designation). The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.), as well as many pathogens, are known, and may be found in NCBI's Genbank database, for example. The second strand of a region is complementary to that region.

The terms "deoxyribonucleic acid" and "DNA", as used herein, refers to a nucleic acid composed primarily or solely of deoxyribonucleotides and can include unnatural nucleotides including Z and P nucleotides.

The terms "ribonucleic acid" and "RNA", as used herein, refer to a nucleic acid composed primarily or solely of ribonucleotides and can include unnatural nucleotides including Z and P nucleotides.

"TC chemistry" or "TC RNA" or "TC amidites" refers to the composition and methods of using RNA monomeric nucleotide precursors protected on the 2'-hydroxyl moiety by a thionocarbamate protecting group to synthesize unmodified RNA or modified RNA comprising one or more modified nucleotides and described in Dellinger et al., J. Am. Chem. Soc. 2011, 133, 11540; U.S. Pat. No. 8,202,983; and U.S. patent application Ser. No. 13/485,592, the contents of which are hereby incorporated by reference herein in their entireties.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or a protecting group or replaced with another atom, e.g., a sulfur atom, or the nitrogen atom of a mono- or di-alkyl amino group.

The phrase "protecting group", as used herein, refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. In general practice, a protecting group should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

The term "halogen", as used herein, refers to fluorine, chlorine, bromine, or iodine.

The term, "linkage", as used herein, refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

The term "functionalized", as used herein, refers to a process whereby a material is modified to have a specific moiety bound to the material, e.g., a molecule or substrate is modified to have the specific moiety; the material (e.g. molecule or support) that has been so modified is referred to as a functionalized material (e.g., functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group. For example, when an alkyl group has a "R" group and R is hydrogen, the alkyl group is considered unsubstituted at the marked location, whereas when that hydrogen is replaced with a halogen, it is considered substituted by a halogen at that location.

The term "substituent", as used herein, refers to a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate, and the like), hydrocarbyl groups, and hydrocarbyl groups substituted with one or more heteroatoms.

Examples of substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Isolated" or "purified" generally refers to isolation of a substance (compound, polynucleotide, protein, polypeptide, polypeptide, chromosome, etc.) such that the substance is a substantial portion of the sample in which it resides (excluding solvents), i.e., greater than the substance is typically found in its natural or un-isolated state. Typically, a substance is a substantial portion of the sample when it represents at least about 1%, at least about 5%, at least about 10%, at least about 20%, at least about 30%, at least about 50%, preferably at least about 80%, or more preferably at least about 90% of the sample (excluding solvents). For example, a sample of isolated RNA will typically include at least about 5% total RNA, where percent is calculated in this context as mass (e.g., in micrograms) of total RNA in the sample divided by mass (e.g., in micrograms) of the sum of (total RNA+other constituents in the sample (excluding solvent). Techniques for purifying polynucleotides and polypeptides of interest are well known in the art and include, for example, gel electrophoresis, ion-exchange chromatography, affinity chromatography, flow sorting, and sedimentation according to density. In typical embodiments, one or more of the nucleotide composition(s) is in isolated form; more typically, all three are obtained in isolated form prior to use in the present methods.

As used herein, $(C_x-C_y)$ refers in general to groups that have from x to y (inclusive) carbon atoms. Therefore, for example, $C_1-C_6$ refers to groups that have 1, 2, 3, 4, 5, or 6 carbon atoms, which encompass $C_1-C_2$, $C_1-C_3$, $C_1-C_4$, $C_1-C_5$, $C_2-C_3$, $C_2-C_4$, $C_2-C_5$, $C_2-C_6$, and all like combinations. $(C_1-C_{20})$ and the like similarly encompasses the various combinations between 1 and 20 (inclusive) carbon atoms, such as $(C_1-C_6)$, $(C_1-C_{12})$ and $(C_3-C_{12})$.

The term "electron-withdrawing group" refers to a moiety that has a tendency to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry, pages 251-59, McGraw Hill Book Company, New York, (1977). Electron-withdrawing groups include nitro, acyl, formyl, sulfonyl, trifluoromethyl, cyano, chloride, and the like.

The term "electron-donating group" refers to a moiety that has a tendency to repel valence electrons from neighboring atoms (i.e., the substituent is less electronegative with respect to neighboring atoms). Electron-donating groups include amino, methoxy, alkyl (including C1-6 alkyl that can have a linear or branched structure), C4-9 cycloalkyl, and the like.

The terms "covalent" or "covalently", as used herein, refer to the nature of a chemical bonding interaction between atoms. A covalent bond is a chemical bonding that involves the sharing of electron pairs between atoms. The stable balance of attractive and repulsive forces between atoms when they share electrons is referred to as covalent bonding. The sharing of electrons allows each atom to attain the equivalent of a full outer shell, corresponding to a stable electronic configuration. Covalent bonding includes various kinds of interactions, e.g., σ-bonding, π-bonding, metal-to-metal bonding, agnostic interactions, and three-center two-electron bonds.

The terms "non-covalent" or "non-covalently", as used herein, refer to the nature of a chemical bonding interaction between atoms. A non-covalent bond is a type of chemical bonding that does not involve the sharing of pairs of electrons, but rather involves more dispersed variations of electromagnetic interactions. There are four commonly mentioned types of non-covalent interactions: hydrogen bonds, ionic bonds, van der Waals forces, and hydrophobic interactions.

The terms "purified" or "to purify", as used herein, refer to the removal of components (e.g., contaminants) from a sample.

"$^1$H NMR" and "$^{31}$P NMR" refer to proton (H) Nuclear Magnetic Resonance and phosphorus (P) Nuclear Magnetic Resonance, respectively, as is known in the art.

DETAILED DESCRIPTION

Embodiments described herein detail a unique methodology and protecting groups that enable synthesis of oligonucleotides having one or more Z nucleotides in an easy, clean and site-specific fashion with high yield. In particular, the method causes little or no damage to oligonucleotide product and little or no modification of the Z nucleotide itself. The invention provides a viable protection strategy for efficient synthesis of long oligonucleotides with at least one Z nucleotide incorporated therein.

In an effort to expand the genetic code and overcome the limitations set by the limited number of naturally occurring nucleotides in standard nucleic acids, a "Z-P" system was developed in which the Z nucleotide can pair with the synthetic nucleotide P via 3 hydrogen bonds. In order for the proposed unnatural base pair to serve as components of the expanded genetic code, a methodology that allows the easy, clean and site-specific incorporation of the unnatural nucleotides into DNA and RNA molecules is essential.

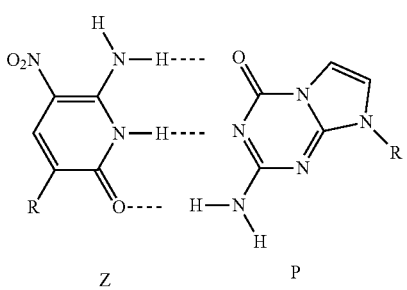

Z                    P

Oligonucleotide synthesis of desired length and sequence with defined chemistry is a fundamental criterion in both laboratory research and applications in molecular biology and medicine. Chemical synthesis of oligonucleotides provides a rapid and inexpensive access to custom-made oligonucleotides of the desired sequence. To prevent undesired side reactions, select functional groups present in nucleosides have to be rendered unreactive or "protected" by attaching protecting groups. The protecting groups are then removed to yield the desired oligonucleotides upon the completion of a particular synthetic step or at the end of the oligonucleotide chain assembly.

Chemical synthesis of oligonucleotide is typically carried out in 3' to 5' direction as solid-phase synthesis using a phosphoramidite method and phosphoramidite building blocks derived from protected 2'-deoxynucleosides (dA, dC, dG, and T), ribonucleosides (A, C, G, and U), or chemically modified nucleosides, e.g., 2'-O-methyl, 2'-F, 2'-MOE (methoxyethoxy), LNA, UNA, etc. To synthesize oligonucleotides, the building blocks are sequentially coupled to the growing oligonucleotide chain in the desired order. Once the chain assembly is complete, the product is released from the solid phase to solution, de-protected, and collected. (U.S. Pat. No. 4,415,732; McBride, et al. 1983 *Tetrahedron Letters* 24:245-248; Sinha, et al. 1984 *Nuc. Acids Res.* 12:4539-4557.)

For example, the 3' position may be protected by $R_3$, e.g., (β-cyanoethyl)-N,N-diisopropyl phosphoramidite or by methyl-N,N-diisopropylphosphoramidite. The hydroxyl at the 3' position may be functionalized by a phosphoramidite group of the general formula: $R_3$: $P(NQ_2)-OR_6$

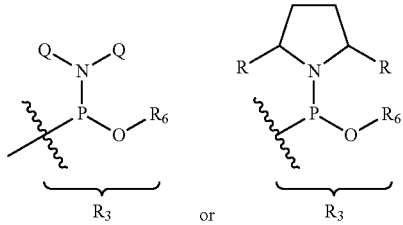

wherein Q is a straight-, branched-, saturated- or unsaturated-alkyl, or aryl, preferably an isopropyl. Alternatively, $NQ_2$ may form a pyrrolidine cyclic ring optionally substituted with an alkyl R group, $R_6$ is a methyl or β-cyanoethyl. Preferably $R_3$ is (β-cyanoethyl)-N,N-diisopropyl phosphoramidite.

The 5' position may be protected by a $R_5$ protecting group such as for example 4,4'-dimethoxytrityl (DMT), monomethoxytrityl (MMT), trimethoxytrityl (TMT), trityl (Tr), or substituted derivatives thereof, or 9-phenylxanthyl (Px). Alternatively, in case the synthesis of the oligonucleotide in the opposite direction is desired, the 5' OH can be functionalized with $R_3$ and the 3'OH protected by $R_5$. When synthesizing oligonucleotides containing one or more Z ribonucleotides, the hydroxyl at the 2' position may be protected by $R_2$ such as $OR_2$ as for example tert-butyldimethylsilyl (TBDMS); a thionocarbamate group such as -1,1-dioxo-thiomorpholine-4-carbothioate (TC); an orthoester group such as bis(2-acetoxyethoxy)methyl (ACE), tri-isopropylsilyloxymethyl (TOM), pivaloyloxymethyl (PivOM), 1-(2-cyanoethoxy)ethyl (CEE), or 2-cyanoethoxymethyl (CEM); an ester group —CO—R; or $CH_2$—CH=$CH_2$, —$CH_2$—O—$CH_2$-phenyl-$NO_2$, —$CH_2$—O—$CH_2$—$CH_2$—$SO_2$-aryl, —$CH_2$—S—S—X, or —$SiR_3$, wherein R is independently selected from straight-, branched-, saturated-, unsaturated, substituted- or unsubstituted-: alkyl, aryl, alkaryl, or aralkyl. $R_2$ may also be a substituted- or unsubstituted-: alkyl, alkoxy (e.g., $CH_2$—$CH_2$—O—$CH_3$), aryl, alkaryl, or aralkyl. Alternatively, $R_2$ may replace $OR_2$ and be H, $OCH_3$ or a halogen.

One of the few reported protecting groups used for the Z nucleotide base (at the 2 position of the pyridone heterocycle) in oligonucleotide synthesis is a para-nitro phenylethyl (NPE) protecting group, as shown in the structure below.

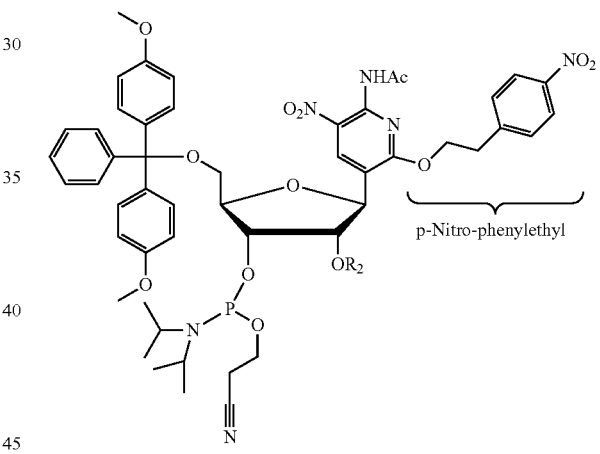

Extensive experimentation, however, revealed that this para-nitrophenylethyl protecting group causes a number of drawbacks. According to a reported protocol (Z. Yang, et al., *Nucleic Acids Research*, 2006, Vol. 34, No. 21, pages 6095-6101) for the deprotection of DNA containing Z nucleotide, the deprotection/cleavage starts with the initial removal of the NPE protecting group in 1M (15%) 1,8-diazabicyclo[5,4,0]undec-7-ene (DBU) overnight at room temperature. Then, in order to deprotect the other protecting groups from the oligonucleotide, the crude sample is subjected to a 5 hr treatment in ethylenediamine (EDA) to complete the deprotection. NPE removal is necessary to prevent EDA substitution of NPE. Yang et al. found that the DBU treatment caused rapid degradation of the RNA sequence.

Thus, the reported protecting strategy gives rise to significantly damaged oligonucleotide product, which in turn results in very low yield of the desired oligonucleotide. In addition, the Z nucleotide in the product is often modified due to EDA substitution.

In short, there is currently no viable protection strategy for efficient synthesis of oligonucleotides incorporating Z nucleotide, which severely restricts the utility of the Z-P unnatural base pair.

Embodiments described herein provide novel protecting groups and methodologies for reliable synthesis of nucleic acid molecules of greater length than those produced by conventional techniques, while achieving acceptable purity and yield.

As described herein, the protecting group, "AcOM" (i.e., Acetyl-Oxy-Methyl, shown below) gives an unexpectedly very high yield of oligonucleotide synthesis as well as a very clean deprotection reaction, leading to no degradation of the RNA or base substitution on the Z base. AcOM enables the synthesis of long oligonucleotides, especially DNAs and RNAs (including Z nucleotides), and in particular, synthesized long RNAs.

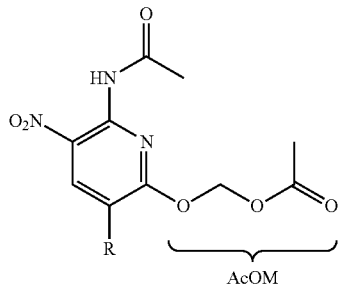

wherein R represents the rest of the protected nucleotide molecule.

While AcOM works best for the protection of 6-amino-3-β-D-ribofuranosyl-5-nitro-2(1H)-pyridone in the synthesis of oligonucleotide containing Z nucleotide(s), as described herein, isobutyryloxymethyl (iBuOM) also works, albeit with some degree of substitution by EDA. Alternative protecting groups or functional groups can also be used in placed of the acetyl on the 6-amino group on the pyridine heterocycle. For example, other electron withdrawing groups may be used in place of the nitro as shown in the general structure below:

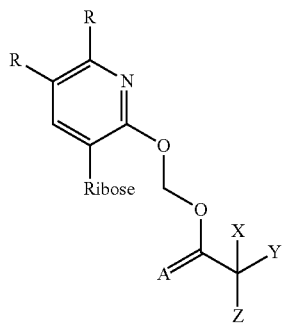

wherein $R_1$ is an electron withdrawing group including without limitation nitro $NO_2$ and cyano CN, F, $C_1$-$C_4$ perfluoroalkyl;

A is O or S;

R is a primary or secondary protected amino group of the formula N=C(R')NR'$_2$ or N(R')COR' or N(COR')$_2$, wherein each R' is independently selected from H, linear-, branched-, saturated- or unsaturated-alkyl, aryl, alkaryl or aralkyl; or wherein R is a protected amino group of the formula N=CR'NR'$_2$, wherein NR'$_2$ is joined to form a 5-8 membered ring wherein said ring can contain a heteroatom selected from O or S; and each of X, Y and Z is independently H, halogen, or a $C_1$-$C_3$ alkyl, wherein two or more of X, Y and Z may together form a 5-8 membered saturated, un-saturated or aryl ring, for example, a phenyl as shown in the exemplary structures (r) to (u) below:

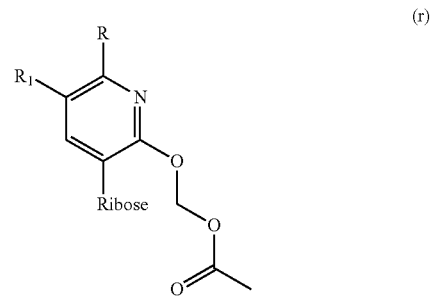

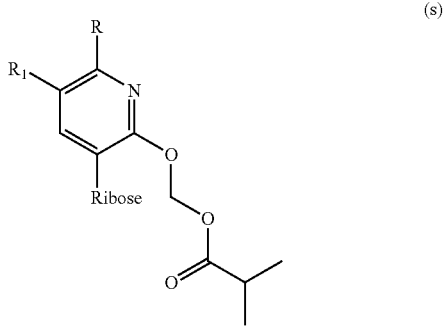

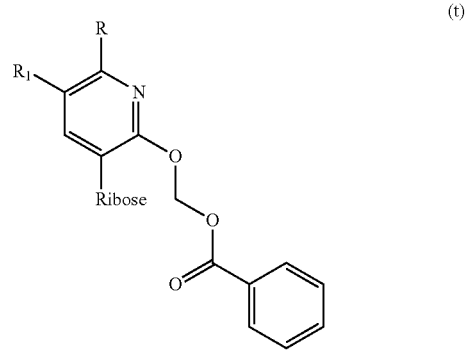

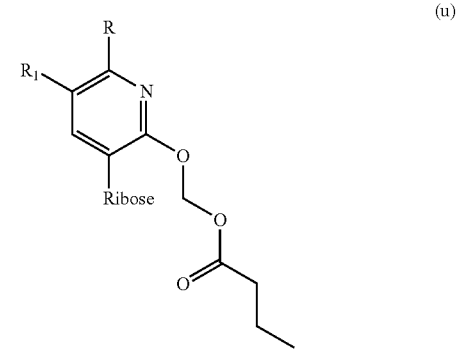

wherein, for example, R can be a protected amino group of the formula N=C(R')NR'$_2$ or, as shown in exemplary structures (v) to (z) below, R can be a protected amino group of the formula N(R')COR' or N(COR')$_2$.

(v)
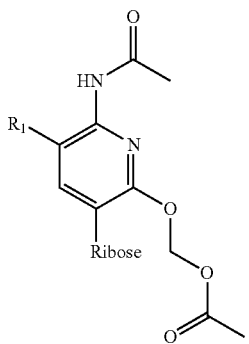

(w)
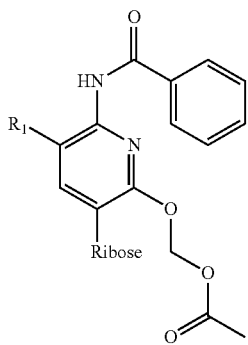

(x)
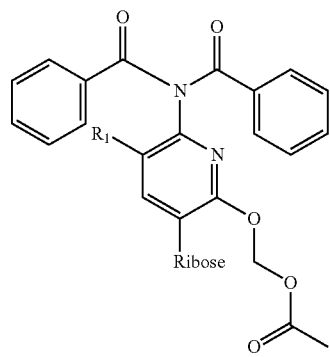

(y)
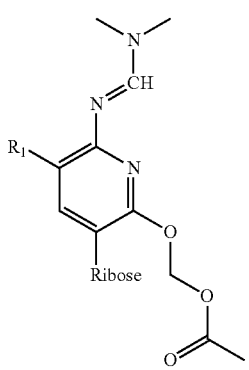

-continued (z)
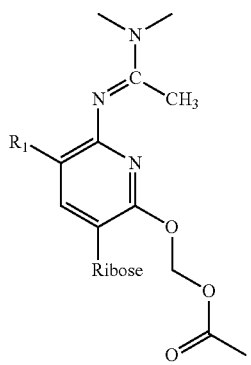

Another advantage of embodiments of the disclosed methodology is that deprotection is a one-step process performed at the end of the oligonucleotide synthesis to both cleave the oligonucleotide from the solid support and remove all the protecting groups. In contrast to procedures in which the deprotection is a two-step process (e.g., initial removal of NPE by DBU treatment, followed by deprotection with EDA as described in Yang et al. above), embodiments of the method described herein perform the deprotection in a single step, e.g., a single base treatment when $R_2$ is H, $OCH_3$, F, TC or pivaloyloxymethyl (PivOM).

In one aspect, the invention generally relates to a compound having the structural formula (I):

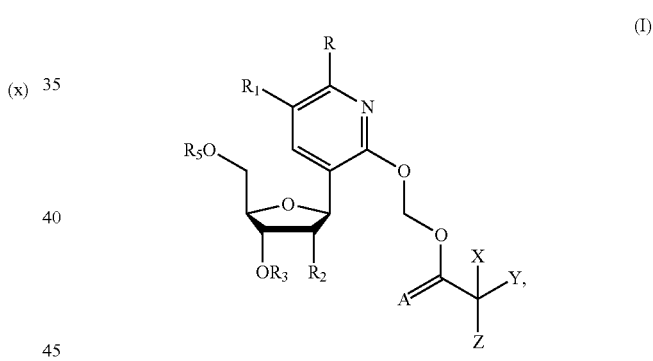

wherein
$R_1$ is $NO_2$ CN, F or $C_1$-$C_4$ perfluoroalkyl;
A is O or S;
$R_2$ is a H, halogen, O-methyl or $OR_{2'}$ wherein $R_{2'}$ is a first protecting group;
$R_3$ is a second protecting group or a phosphoramidite group;
$R_5$ is a third protecting group; and
R is a primary or secondary protected amino group of the formula $N=C(R')NR'_2$ or $N(R')COR'$ or $N(COR')_2$, wherein each R' is independently selected from H, linear-, branched-, saturated- or unsaturated-alkyl, aryl, alkaryl or aralkyl; or wherein R is a protected amino group of the formula $N=CR'NR'_2$, wherein $NR'_2$ may be joined to form a 5-8 membered ring wherein said ring can contain a heteroatom selected from O or S.

In certain embodiments, $R_2$ is H.
In certain embodiments, $R_2$ is $OR_{2'}$. In certain embodiments, $R_{2'}$ is 1,1-dioxo-thiomorpholine-4-carbothioate (TC). In certain embodiments, $R_{2'}$ is tert-butyldimethylsilyl (TBDMS), tri-iso-propylsilyloxymethyl (TOM), bis(2-acetoxyethoxy)methyl (ACE), pivaloyloxymethyl (PivOM), 1-(2-cyanoethoxy)ethyl (CEE), 2-cyanoethoxymethyl (CEM), —CO—R″, CH$_2$—CH=CH$_2$, CH$_2$—O—CH$_2$-phenyl-NO$_2$, CH$_2$—S—S—R$_1$, or Si(R″)$_3$; wherein R″ is independently selected from straight-, branched-, saturated or unsaturated-alkyl, aryl, alkaryl, or aralkyl.

In certain embodiments, R$_3$ is (β-cyanoethyl)-N,N-diisopropyl phosphoramidite. In certain embodiments, R$_3$ is methyl-N,N-diisopropylphosphoramidite or (β-cyanoethyl)-N-pyrrolidino phosphoramidite.

In certain embodiments, R$_5$ is 4,4'-dimethoxytrityl (DMT). In certain embodiments, R$_5$ is monomethoxytrityl (MMT), trimethoxytrityl (TMT) or 9-phenylxanthyl (Px).

In certain preferred embodiments, R$_3$ is (β-cyanoethyl)-N,N-diisopropyl phosphoramidite, and R$_5$ is DMT.

In certain preferred embodiments R is acetyl, R$_1$ is NO$_2$, A is O, R$_2$ is 1,1-dioxo-thiomorpholine-4-carbothioate (TC), R$_3$ is (β-cyanoethyl)-N,N-diisopropyl phosphoramidite, R$_5$ is DMT, and each of X, Y, and Z is H.

In certain preferred embodiments R is acetyl, R$_1$ is CN, A is O, R$_2$ is 1,1-dioxo-thiomorpholine-4-carbothioate (TC), R$_3$ is (β-cyanoethyl)-N,N-diisopropyl phosphoramidite, R$_5$ is DMT, and each of X, Y, and Z is H.

In certain preferred embodiments R is acetyl, R$_1$ is NO$_2$, A is O, R$_2$ is 1,1-dioxo-thiomorpholine-4-carbothioate (TC), R$_3$ is (β-cyanoethyl)-N,N-diisopropyl phosphoramidite, R$_5$ is DMT, each of X and Y is methyl, and Z is H.

In certain preferred embodiments R is acetyl, R$_1$ is CN, A is O, R$_2$ is 1,1-dioxo-thiomorpholine-4-carbothioate (TC), R$_3$ is (β-cyanoethyl)-N,N-diisopropyl phosphoramidite, R$_5$ is DMT, each of X and Y is methyl, and Z is H.

In certain preferred embodiments, the compound has the structural formula (II) or (III) below:

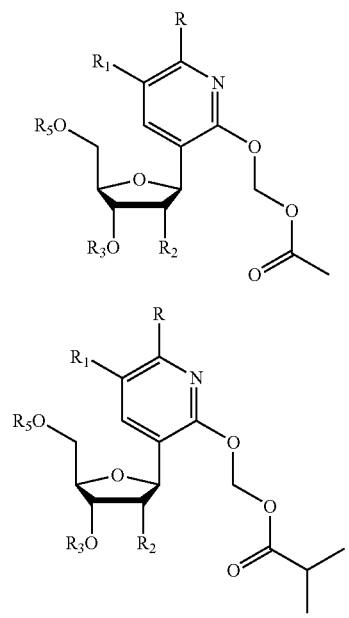

wherein R$_1$, R$_2$, R$_3$, R$_4$ and R are defined as described above for a compound of formula (I).

In certain preferred embodiments of the compounds of formula (II) and (III), R$_2$ is a OR$_{2'}$, wherein R$_{2'}$ 1,1-dioxo-thiomorpholine-4-carbothioate (TC) protecting group of the following formula:

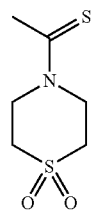

In certain preferred embodiments of the compounds of formula (II) and (III), R$_5$ is a dimethoxytrityl (DMT) and R$_3$ is a phosphoramidite defined as —P(NQ$_2$)—OR$_6$

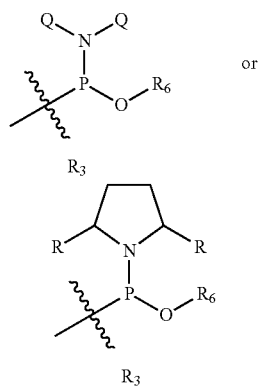

wherein Q is a straight, branched, saturated or unsaturated alkyl or aryl, preferably an isopropyl. Alternatively, NQ$_2$ may form a pyrolidine cyclic ring optionally substituted with an alkyl R group. R$_6$ is a methyl or β-cyanoethyl. Preferably R$_3$ is (β-cyanoethyl)-N,N-diisopropyl phosphoramidite.

In certain preferred embodiments, the compound has the formula (IV) shown below:

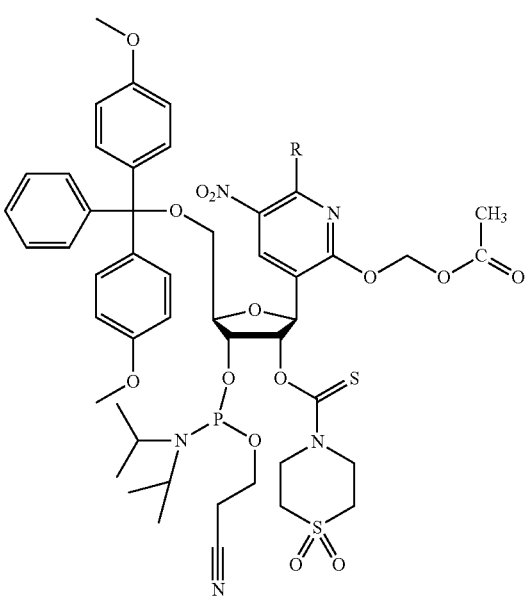

In yet another aspect, the invention generally relates to an oligonucleotide, wherein at least one of the nucleotides has the structural formula (V) below:

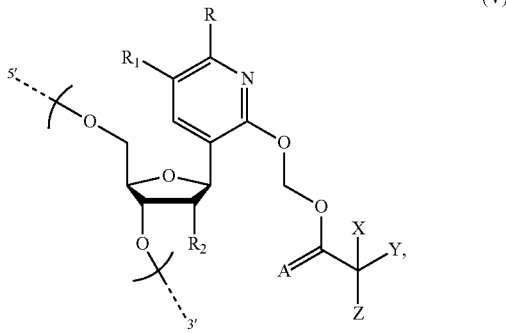

(V)

wherein
$R_1$ is an electron withdrawing group;
A is O or S; and
$R_2$ is 1,1-dioxo-thiomorpholine-4-carbothioate (TC), tert-butyldimethylsilyl (TBDMS), tri-iso-propylsilyloxymethyl (TOM), bis(2-acetoxyethoxy) methyl (ACE), pivaloyloxymethyl (PivOM), 1-(2-cyanoethoxy)ethyl (CEE), 2-cyanoethoxymethyl (CEM), —CO—R", —$CH_2$—CH=$CH_2$, —$CH_2$—O—$CH_2$-phenyl-$NO_2$, —$CH_2$—O—$CH_2$—$CH_2$—$SO_2$-aryl, $CH_2$—S—S—$R_1$, or —Si(R")$_3$; wherein R" is independently selected from straight-, branched-, saturated or unsaturated-alkyl, aryl, alkaryl, or aralkyl;
R is a protected amino group of the formula N=C(R')NR'$_2$ or N(R')COR' or N(COR')$_2$ wherein each R' is independently selected from H, linear-, branched-, saturated- or unsaturated-alkyl, aryl, alkaryl or aralkyl; or wherein R is a protected amino group of the formula N=CR'NR'$_2$, NR'$_2$ may be joined to form a 5-8 membered ring wherein said ring can contain a heteroatom selected from O or S; and
each of X, Y and Z is independently H, halogen, or a $C_1$-$C_3$ alkyl, wherein two or more of X, Y and Z may together form a 5-8 membered saturated, un-saturated or aryl ring.

In certain embodiments, $R_2$ is 1,1-dioxo-thiomorpholine-4-carbothioate (TC). In certain embodiments, $R_2$ is PivOM. In certain embodiments, $R_2$ is H, $OCH_3$ or F.

In certain embodiments, $R_1$ is $NO_2$, R is $CH_3$, and each of X, Y and Z is H. In certain embodiments, $R_2$ is 1,1-dioxo-thiomorpholine-4-carbothioate (TC).

In certain embodiments, two or more (e.g., 2, 3, 4, 5, 10, 20, 50 or more) of the nucleotides of oligonucleotide has the structural formula (IV).

Aspects of the present disclosure include methods for synthesizing an oligonucleotide using one or more compounds of formulas I to IV above are disclosed herein. The synthesized oligonucleotide may be a DNA, an RNA or a mixed sequence of DNA and RNA including one or more unnatural nucleotides. The synthesized oligonucleotide has a length of about 3-mer to about 1,000-mer (e.g., inter alia, about 5-mer to about 1,000-mer, about 10-mer to about 1,000-mer, about 20-mer to about 1,000-mer, about 3-mer to about 300-mer, about 5-mer to about 300-mer, about 10-mer to about 300-mer, about 20-mer to about 300-mer, about 3-mer to about 100-mer, about 5-mer to about 100-mer, about 10-mer to about 100-mer, about 20-mer to about 100-mer, about 3-mer to about 50-mer, about 5-mer to about 50-mer, about 10-mer to about 50-mer, about 3-mer to about 30-mer, about 10-mer to about 30-mer).

In yet another aspect, embodiments of a method for synthesizing an oligonucleotide are provided. The method includes: protecting an unnatural nucleotide with an acetyl-oxy-methyl group, incorporating the protected unnatural nucleotide into a nucleotide sequence; and
removing the acetyl-oxy-methyl group from the unnatural nucleotide incorporated into the nucleotide sequence. The protected unnatural nucleotide has the structural formula (V),

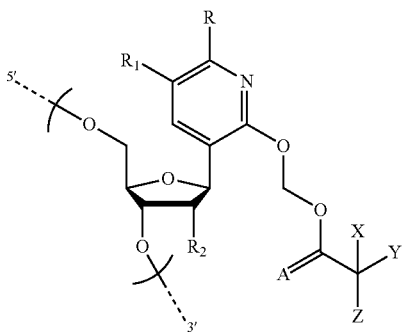

(V)

wherein
$R_1$ is an electron withdrawing group,
A is O or S,
$R_2$ is 1,1-dioxo-thiomorpholine-4-carbothioate (TC), tert-butyldimethylsilyl (TBDMS), tri-iso-propylsilyloxymethyl (TOM), bis(2-acetoxyethoxy)methyl (ACE), pivaloyloxymethyl (PivOM), 1-(2-cyanoethoxy)ethyl (CEE), 2-cyanoethoxymethyl (CEM), —CO—R", —$CH_2$—CH=$CH_2$, —$CH_2$—O—$CH_2$-phenyl-$NO_2$, —$CH_2$—O—$CH_2$—$CH_2$—$SO_2$-aryl, $CH_2$—S—S—$R_1$, or —Si(R")$_3$; wherein R" is independently selected from straight-, branched-, saturated or unsaturated-alkyl, aryl, alkaryl, or aralkyl;
R is a protected amino group of the formula N=C(R')NR'$_2$ or N(R')COR' or N(COR')$_2$ wherein each R' is independently selected from H, linear-, branched-, saturated- or unsaturated-alkyl, aryl, alkaryl or aralkyl; or wherein R is a protected amino group of the formula N=CR'NR'$_2$, wherein NR'$_2$ is joined to form a 5-8 membered ring wherein said ring can contain a heteroatom selected from O or S; and
each of X, Y and Z is independently H, halogen, or a $C_1$-$C_3$ alkyl, wherein two or more of X, Y and Z may together form a 5-8 membered saturated, un-saturated or aryl ring.

In certain embodiments, $R_2$ is 1,1-dioxo-thiomorpholine-4-carbothioate (TC). In certain embodiments, $R_2$ is PivOM.

In certain embodiments, $R_1$ is $NO_2$, R is $CH_3$, each of X, Y and Z is H, and $R_2$ is 1,1-dioxo-thiomorpholine-4-carbothioate (TC).

The oligonucleotide may be DNA, RNA or a mixed sequence of DNA and RNA.

In certain embodiments, removing the acetyl-oxy-methyl group is accomplished with a one-step reaction with a base.

In certain embodiments, the base is selected from a reagent comprising ethylenediamine, or a reagent comprising ammonia or methylamine or a combination thereof. In certain embodiments, removing all the protecting groups from the oligonucleotide including the acetyl-oxy-methyl group or the isobutyryl-oxy-methyl group and cleaving the oligonucleotide from the solid support is accomplished in a one-step reaction with a base. When $R_2$ is TC, H, O-methyl or F, the reagent used to deprotect the oligonucleotide including the acetyl-oxy-methyl group or the isobutyryl-oxy-methyl group and to cleave the oligonucleotide from the solid support, comprises ethylenediamine. When $R_2$ is PivOM, H, O-methyl or F, the reagent used to deprotect the oligonucleotide including the acetyl-oxy-methyl group or the isobutyryl-oxy-methyl group and to cleave the oligonucleotide from the solid support, comprises ammonia or methylamine.

The synthesized oligonucleotide is of a length of about 3-mer to about 1,000-mer (e.g., about 5-mer to about 1,000-mer, about 10-mer to about 1,000-mer, about 20-mer to about 1,000-mer, about 3-mer to about 300-mer, about 5-mer to about 300-mer, about 10-mer to about 300-mer, about 20-mer to about 300-mer, about 3-mer to about 100-mer, about 5-mer to about 100-mer, about 10-mer to about 100-mer, about 20-mer to about 100-mer, about 3-mer to about 50-mer, about 5-mer to about 50-mer, about 10-mer to about 50-mer, about 3-mer to about 30-mer, about 10-mer to about 30-mer).

In yet another aspect, the invention generally relates to a method for synthesizing an oligonucleotide. The method includes: protecting a nucleotide with an acetyl-oxy-methyl group having the formula:

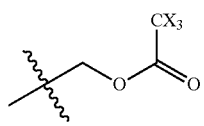

wherein each X is independently H or a halogen; chemically incorporating the protected nucleotide into a nucleotide sequence; and removing the acetyl-oxy-methyl group from the nucleotide incorporated into the nucleotide sequence.

EXAMPLES

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

The process of preparing protected rZ phosphoramidites and their suitability for use in nucleic acid synthesis is described in the Examples below. In Example 1, the preparation of representative protected rZ nucleotides is described. In Examples 2 and 3, the protecting groups para-nitrophenylethyl (NPE) and acetyloxymethyl (AcOM), respectively, are tested. Example 4 describes the synthesis of an oligonucleotide with an incorporated rZ nucleotide, where the rZ ramidite used during the synthesis has an acetyloxymethyl (AcOM) protecting group.

Example 1 Preparation of Protected rZ Phosphoramidites

The flow chart below shows the pathway for production of compounds 1 to 6, the methods for production of which are described thereafter. Note that R comprises structures a, b, c, d, or e for respective compounds. That is, e.g., Compound 2a has R=structure a, Compound 2b has R-structure b, etc.

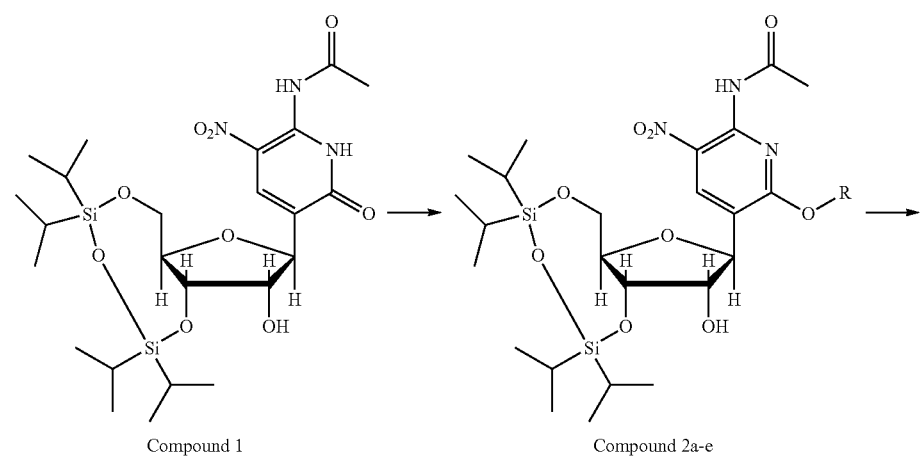

Compound 1            Compound 2a-e

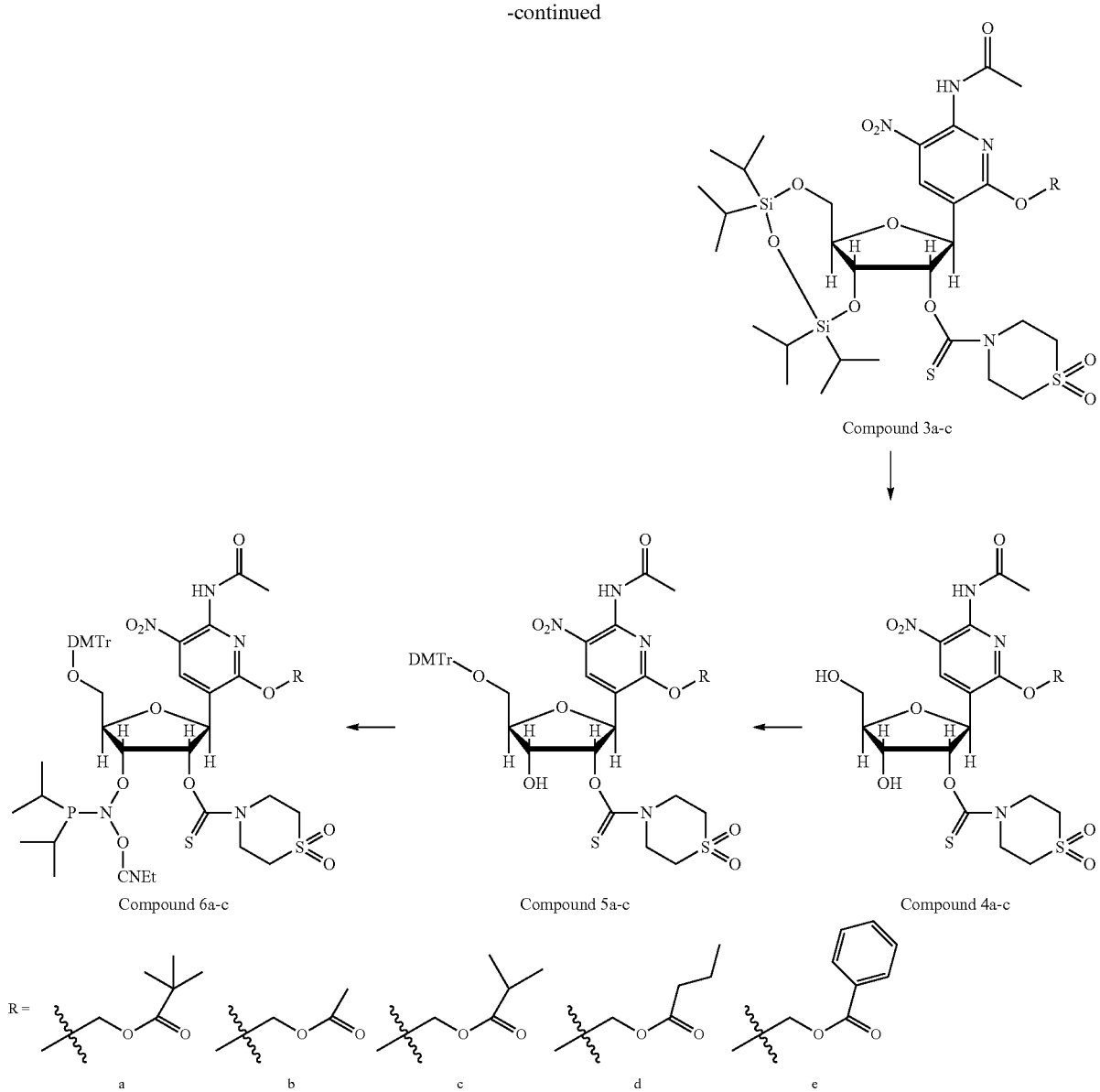

Compound 3a-c

Compound 6a-c  Compound 5a-c  Compound 4a-c

R = a, b, c, d, e

Compound 1: 3',5'-O-(1,1,3,3-tetraisopropyl-1,3-disiloxanediyl)-1'-[6-acetamido-5-nitro-pyridone]-β-D-ribofuranose 3',5'-O-(1,1,3,3-tetraisopropyl-1,3-disiloxanediyl)-1'-[6-acetamido-5-nitro-2-(4-nitrophenethoxy)-pyridone]-β-D-ribofuranose (TIPDS, Ac, NPE protected rZ) was purchased from Firebird Biomolecular Sciences and (4 g, 5.66 mmol) was dissolved in acetonitrile (110 mL) with DBU (8.45 mL, 56.6 mmol). The mixture was stirred overnight and monitored by TLC (3% MeOH:DCM). When complete, the reaction was neutralized with anhydrous acetic acid, evaporated to 20 mL, dissolved in DCM, washed with brine, and back-extracted with DCM. The product was dried, dissolved in minimal DCM, loaded on a silica-gel column, and eluted using a gradient of 1-2% MeOH in DCM. The product was evaporated to a yellow foam, giving 2.8 g, an 88% yield Compound 1.

Compound 2a: 3',5'-O-(1,1,3,3-tetraisopropyl-1,3-disiloxanediyl)-1'-[6-acetamido-5-nitro-2-(pivaloyloxymethyl)-pyridone]-β-D-ribofuranose Compound 1 (1.25 g, 2.19 mmol) was dissolved in ACN (27 mL) with diisopropylethylamine (4.57 mL, 26.2 mmol). Chloromethyl pivalate (3.78 mL, 26.2 mmol) was added slowly and reacted overnight. The reaction was diluted with 10 mL of DCM, washed with brine, and back extract two times with DCM. The product dissolved in 1:1 hexane: dichloromethane, loaded on a silica-gel column, and eluted using a gradient of ethyl acetate from 15-25% in hexanes. The product was evaporated to a clear oil, giving 1.2 g, a 80% yield of Compound 2a. $^1$H NMR (CDCl$_3$) δ: 10.51 (s, 1H, NH), 8.71 (d, 1H, C4), 6.26, 6.11 (dd, 2H, oxymethyl), 5.00 (m, 1H, 1'), 4.24 (m, 1H, 3'), 4.1 (m, 2H, 5'), 4.0 (m, 1H, 4'), 3.94 (m, 1H, 2'), 2.57 (s, 3H, Ac), 1.23 (s, 9H, Piv), 1.05 (m, 28H, TIPDS)

Compound 3a: 2'-O-(1,1-Dioxo-thiomorpholine-4-carbothioate)-3',5'-O-(1,1,3,3-tetraisopropyl-1,3-disiloxanediyl)-1'-[6-acetamido-5-nitro-2-(pivaloyloxmethyl)-pyridone]-β-D-ribofuranose Compound 2a (1.2 g, 1.75 mmol) was dissolved in 10 mL of DCM. 1,1'-thiocarbonyldiimidazole (0.374 g, 2.10 mmol) and a catalytic amount of DMAP were added to the reaction and stirred overnight. The reaction was followed by RP-HPLC on a C18 column using a gradient of 50-100% acetonitrile in 10 min. When the reaction was complete, thiomorpholine-1,1-dioxide (0.31 g, 2.29 mmol) was added and stirred overnight. The reaction mixture was evaporated to dryness, dissolved in 1:1 DCM:hexane, loaded on silica column, and eluted using a gradient of ethyl acetate from 10-40% in hexanes. The product was evaporated to dryness giving 1.37 g, a 91% yield of Compound 3a.

Compound 4a: 2'-O-(1,1-Dioxo-thiomorpholine-4-carbothioate)-1'-[6-acetamido-5-nitro-2-(pivaloyloxmethyl)-pyridone]-β-D-ribofuranose Compound 3a (1.37 g, 1.59 mmol) was dissolved 16 mL of 2-MeTHF and pyridine (1.53 mL, 19.1 mmol). HF (70% in pyridine, 1.53 mL, 19.1 mmol) was added slowly on ice, reacted for 1 hour, and continued at room temperature overnight. The reaction was washed twice with water, back extracted two times with 2-Me-THF, and dried overnight giving 0.97 g, 97% yield of Compound 4a.

Compound 5a: 2'-O-(1,1-Dioxo-thiomorpholine-4-carbothioate)-5'-O-DMTr-1'-[6-acetamido-5-nitro-2-(pivaloyloxymethyl)-pyridone]-β-D-ribofuranose Compound 4a (0.97 g, 1.55 mmol) was dissolved in 15 mL DCM with N-methylmorpholine (0.19 mL, 1.71 mmol). DMT-Cl (0.53 g, 1.55 mmol total) was added in 0.7 equivalent then 0.1 eq portions till the reaction complete as monitored by RP-HPLC on C18 column using a gradient of 0-100% acetonitrile in 10 min. The reaction was washed in water, back extracted with DCM. The product was evaporated to dryness, giving a 1.15 g, a 80% yield of Compound 5a.

Compound 6a: 2'-O-(1,1-Dioxo-thiomorpholine-4-carbothioate)-5'-O-DMTr-1'-[6-acetamido-5-nitro-2-(pivaloyloxymethyl)-pyridone]-3'-[(2-cyanoethyl)-(N,N-diisopropyl)]-phosphoramidite-β-D-ribofuranose Compound 5a (1.15 g, 1.25 mmol) was dissolved in 12 mL of DCM. N-methylmorpholine (0.22 mL, 1.99 mmol) and (2-cyanoethyl)-N,N'-diisopropylchlorophosphoramidite (0.41 mL, 1.97 mmol) was added and stirred for 1 hour. The reaction was washed with bicarb then brine, dried over sulfate and then concentrated to a yellow foam. The product was purified by silica chromatography pre-equilibrated with 10% acetone in hexanes and neutralized with 1% TEA; the excess TEA was removed with 1 column volume of 10% acetone in hexanes. The product was added to the column in minimal DCM and eluted using a gradient of 80:10:10 to 60:10:30 hexane:acetone:ethyl acetate and evaporated to a pale yellow foam. 1.2 g, 85% yield of Compound 6a. $^{31}$P NMR (ACN-d$_3$) δ (PPM): 149.88, 148.52 (diastereomers). $^1$H NMR (CDCl$_3$) δ: 9.90 (s, 1H, NH), 8.71 (m, 1H, C4), 6.85-7.56 (m, 13H, DMT), 6.21, 6.19 (m, 2H, oxymethyl), 5.23 (m, 1H, 1'), 4.6, 4.3 (m, 4H, thiomorpholine), 4.24 (m, 1H, 3'), 4.1 (m, 2H, 5'), 4.0 (m, 1H, 4'), 3.94 (m, 1H, 2'), 4.2, 3.8 (m, 2H, CE), 3.81 (s, 6H, DMT), 3.5 (m, 2H, iPr), 3.2 (m, 4H, thiomorpholine), 2.7 (m, 2H, CE), 2.57 (m, 3H, Ac), 1.3 (m, 12H, iPr), 1.23 (m, 9H, Piv).

Compound 2b: 3',5'-O-(1,1,3,3-tetraisopropyl-1,3-disiloxanediyl)-1'-[6-acetamido-5-nitro-2-(acetyloxymethyl)-pyridone]-β-D-ribofuranose Compound 1 (1 g, 1.75 mmol) was dissolved in ACN (20 mL) with diisopropylethylamine (0.61 mL, 3.5 mmol). Bromomethyl Acetate (0.34 mL, 3.5 mmol) was added slowly and reacted overnight. The reaction was diluted with 10 mL of DCM, washed with brine, and back-extracted two times with DCM. The product was dissolved in 1:1 hexane:dichloromethane, loaded on a silica-gel column, and eluted using a gradient of ethyl acetate from 10-30% in hexanes. The product was evaporated to a clear oil, giving 1.1 g, a 97% yield of Compound 2b. $^1$H NMR (CDCl$_3$) δ: 10.51 (s, 1H, NH), 8.72 (s, 1H, C4), 6.20, 6.15 (dd, 2H, oxymethyl), 5.02 (m, 1H, 1'), 4.26 (m, 1H, 3'), 4.2 (m, 2H, 5'), 4.0 (m, 1H, 4'), 3.96 (m, 1H, 2'), 2.52 (s, 3H, AcN), 2.14 (s, 3H, AcO), 1.05 (m, 28H, TIPDS).

Compound 3b: 2'-O-(1,1-Dioxo-thiomorpholine-4-carbothioate)-3',5'-O-(1,1,3,3-tetraisopropyl-1,3-disiloxanediyl)-1'-[6-acetamido-5-nitro-2-(acetyloxmethyl)-pyridone]-β-D-ribofuranose Compound 2b (1.1 g, 1.71 mmol) was dissolved in 10 mL of DCM. 1,1'-thiocarbonyldiimidazole (0.365 g, 2.05 mmol) and a catalytic amount of DMAP were added to the reaction and stirred overnight. The reaction was followed by RP-HPLC on a C18 column using a gradient of 50-100% acetonitrile in 10 min. When the reaction was complete, thiomorpholine-1,1-dioxide (0.30 g, 2.23 mmol) was added and stirred overnight. The reaction mixture was evaporated to dryness, dissolved in 1:1 DCM:hexane, loaded on silica column, and eluted using a gradient of ethyl acetate from 10-40% in hexanes. The product was evaporated to dryness giving 1.37 g, a 74% yield of Compound 3b.

Compound 4b: 2'-O-(1,1-Dioxo-thiomorpholine-4-carbothioate)-1'-[6-acetamido-5-nitro-2-(acetyloxmethyl)-pyridone]-β-D-ribofuranose Compound 3b (1.02 g, 1.24 mmol) was dissolved 12 mL of 2-MeTHF and pyridine (1.2 mL, 14.9 mmol). HF (70% in pyridine, 0.37 mL, 14.9 mmol) was added slowly on ice, reacted for 15 min, and continued at room temperature for 6 hours. The reaction was washed twice with water, back extracted two times with 2-Me-THF, and dried overnight giving 0.7 g, 98% yield of Compound 4b.

Compound 5b: 2'-O-(1,1-Dioxo-thiomorpholine-4-carbothioate)-5'-O-DMTr-1'-[6-acetamido-5-nitro-2-(acetyloxmethyl)-pyridone]-β-D-ribofuranose Compound 4b (0.7 g, 1.2 mmol) was dissolved in 12 mL DCM with N-methylmorpholine (0.15 mL, 1.33 mmol). DMT-Cl (0.41 g, 1.2 mmol total) was added in 0.7 equivalent then in 0.1 eq. portions until the reaction complete as monitored by RP-HPLC on C18 column using a gradient of 0-100% acetonitrile in 10 min. The reaction was washed in water, back extracted with DCM. Crude product was purified on silica column that was equilibrated in hexanes with 1% NMM and washed with 2 column volumes of hexanes. The product was eluted using a gradient of ethyl acetate from 10-40% in hexanes and dried overnight to give 1.1 g, a 95% yield of Compound 5b.

Compound 6b (2'-O-(1,1-Dioxo-thiomorpholine-4-carbothioate)-5'-O-DMTr-1'-[6-acetamido-5-nitro-2-(acetyloxmethyl)-pyridone]-3'-[(2-cyanoethyl)-(N,N-diisopropyl)]-phosphoramidite-β-D-ribofuranose.)

Compound 5b (1.1 g, 1.15 mmol) was dissolved in 11 mL of DCM. N-methylmorpholine (0.20 mL, 1.84 mmol) and (2-cyanoethyl)-N,N'-diisopropylchlorophosphoramidite (0.38 mL, 1.72 mmol) was added and stirred for 1 hour. The reaction was washed with bicarb then brine, dried over sulfate and then concentrated to a yellow foam. The product was purified by silica chromatography pre-equilibrated with 10% acetone in hexanes and neutralized with 1% TEA; the excess TEA was removed with 1 column volume of 10% acetone in hexanes. The product added to the column in minimal DCM and eluted using a gradient of 80:10:10 to 60:10:30 hexane:acetone:ethyl acetate and evaporated to a pale yellow foam. 0.82 g, 66% yield of Compound 6b. $^{31}$P NMR (ACN-d$_3$) δ (PPM): 149.86, 148.48. $^1$H NMR (CDCl$_3$) δ: 9.91 (s, 1H, NH), 8.69 (m, 1H, C4), 6.89-7.54 (m, 13H, DMT), 6.18, 5.98 (dd, 2H, oxymethyl), 5.28 (m, 1H, 1').

Compound 2c: 3',5'-O-(1,1,3,3-tetraisopropyl-1,3-disiloxanediyl)-1'-[6-acetamido-5-nitro-2-(isobutyryloxmethyl)-pyridone]-β-D-ribofuranose Compound 1 (1 g, 1.75 mmol) was dissolved in ACN (20 mL) with diisopropylethylamine (3.66 mL, 21 mmol). Chloromethyl isobutyrate (2.65 mL, 21 mmol) was added slowly and reacted overnight. The reaction was diluted with 10 mL of DCM, washed with brine, and back extract two times with DCM. The product dissolved in 1:1 hexane:dichloromethane, loaded on a silica-gel column, and eluted using a gradient of ethyl acetate from 20-30% in hexanes. The product was evaporated to a clear oil, giving 0.73 g, a 62%% yield of Compound 2c. $^1$H NMR (CDCl$_3$) δ: 10.51 (s, 1H, NH), 8.71 (s, 1H, C4), 6.25, 6.13 (dd, 2H, oxymethyl), 5.01 (m, 1H, 1'), 4.26 (m, 1H, 3'), 4.2 (m, 2H, 5'), 4.0 (m, 1H, 4'), 3.96 (m, 1H, 2'), 2.63 (m, 1H, iBu), 2.55 (s, 3H, AcN), 1.2 (m, 6H, iBu), 1.05 (m, 28H, TIPDS).

Compound 3c: 2'-O-(1,1-Dioxo-thiomorpholine-4-carbothioate)-3',5'-O-(1,1,3,3-tetraisopropyl-1,3-disiloxanediyl)-1'-[6-acetamido-5-nitro-2-(isobutyryloxmethyl)-pyridone]-β-D-ribofuranose Compound 2c (0.73 g, 1.09 mmol) was dissolved in 10 mL of DCM. 1,1'-thiocarbonyldiimidazole (0.233 g, 1.3 mmol) and a catalytic amount of DMAP was added to the reaction and stirred for 48 hours. The reaction was followed by RP-HPLC on a C18 column using a gradient of 50-100% acetonitrile in 10 min. When the reaction was complete, thiomorpholine-1,1-dioxide (0.20 g, 1.5 mmol) was added and stirred overnight. The reaction mixture was evaporated to dryness, dissolved in 1:1 DCM:hexane, loaded on silica column, and eluted using a gradient of ethyl acetate from 10-40% in hexanes. The product was evaporated to dryness giving 0.78 g, an 84% yield of Compound 3c.

Compound 4c: 2'-O-(1,1-Dioxo-thiomorpholine-4-carbothioate)-1'-[6-acetamido-5-nitro-2-(isobutyryloxmethyl)-pyridone]-β-D-ribofuranose Compound 3c (0.78 g, 0.92 mmol) was dissolved 9 mL of 2-MeTHF and pyridine (0.89 mL, 11.0 mmol). HF (70% in pyridine, 0.28 mL, 11.0 mmol) was added slowly on ice, reacted for 15 min, and continued at room temperature for 6 hours. The reaction was washed twice with water, back-extracted two times with 2-Me-THF, and dried overnight giving 0.57 g, 98% yield of Compound 4c.

Compound 5c: 2'-O-(1,1-Dioxo-thiomorpholine-4-carbothioate)-5'-O-DMTr-1'-[6-acetamido-5-nitro-2-(isobutyryloxmethyl)-pyridone]-β-D-ribofuranose Compound 4c (0.57 g, 0.92 mmol) was dissolved in 9 mL DCM with N-methylmorpholine (0.11 mL, 1.01 mmol). DMT-Cl (0.31 g, 0.92 mmol total) was added in 0.7 equivalent and then in 0.1 eq portions until the reaction complete as monitored by RP-HPLC on C18 column using a gradient of 0-100% acetonitrile in 10 min. The reaction was washed in water, and back-extracted with DCM. Crude product was purified on silica column that was equilibrated in hexanes with 1% NMM and washed with 2 column volumes of hexanes. The product was eluted using a gradient of ethyl acetate from 10-40% in hexanes and dried overnight to give 0.8 g, a 87% yield of Compound 5c.

Compound 6c: 2'-O-(1,1-Dioxo-thiomorpholine-4-carbothioate)-5'-O-DMTr-1'-[6-acetamido-5-nitro-2-(isobutyryloxmethyl)-pyridone]-3'-[(2-cyanoethyl)-(N,N-diisopropyl)]-phosphoramidite-β-D-ribofuranose Compound 5c (0.8 g, 0.88 mmol) was dissolved in 9 mL of DCM. N-Methylmorpholine (0.16 mL, 1.41 mmol) and (2-cyanoethyl)-N,N'-diisopropylchlorophosphoramidite (0.29 mL, 1.32 mmol) was added and stirred for 1 hour. The reaction was washed with bicarbonate then brine, dried over sulfate and then concentrated to a yellow foam. The product was purified by silica chromatography, pre-equilibrated with 10% acetone in hexanes, and neutralized with 1% TEA. The excess TEA was removed with 1 column volume of 10% acetone in hexanes. The product added to the column in minimal DCM and eluted using a gradient of 80:10:10 to 50:10:40 hexane:acetone:ethyl acetate and evaporated to a pale yellow foam. 0.44 g, 40% yield of Compound 6c. $^{31}$P NMR (ACN-d$_3$) δ (PPM): 149.79, 148.42.

Compound 2d: 3',5'-O-(1,1,3,3-tetraisopropyl-1,3-disiloxanediyl)-1'-[6-acetamido-5-nitro-2-(butyryloxmethyl)-pyridone]-β-D-ribofuranose Compound 1 (0.155 g, 0.20 mmol) was dissolved in ACN (5 mL) with diisopropylethylamine (0.42 mL, 2.4 mmol). Chloromethyl butyrate (0.31 mL, 2.4 mmol) was added slowly and reacted overnight. The reaction was diluted with 5 mL of DCM, washed with brine, and back-extracted two times with DCM. The product was dissolved in 1:1 hexane:dichloromethane, loaded on a silica-gel column, and eluted using a gradient of ethyl acetate from 10-30% in hexanes. The product was evaporated, giving 0.12 g, an 89% yield of Compound 2d. $^1$H NMR shows two similar products with a 40% contaminant that was not characterized.

Compound 2e: 3',5'-O-(1,1,3,3-tetraisopropyl-1,3-disiloxanediyl)-1'-[6-acetamido-5-nitro-2-(benzoyloxymethyl)-pyridone]-β-D-ribofuranose Compound 1 (0.07 g, 0.12 mmol) was dissolved in ACN (5 mL) with diisopropylethylamine (0.38 mL, 2.2 mmol). Chloromethyl benzoate (0.31 mL, 2.2 mmol) was added slowly and reacted overnight. The reaction was diluted with 10 mL of DCM, washed with brine, and back-extracted two times with DCM. The product was dissolved in 1:1 hexane:dichloromethane, loaded on a silica-gel column, and eluted using a gradient of ethyl acetate from 0-30% in hexanes. The product was evaporated to a clear oil, giving 0.04 g, a 47% yield of Compound 2e. $^1$H NMR shows two similar products including 30% contamination with a different unknown product.

Example 2 Testing of Para-Nitrophenylethyl (NPE) as rZ Protecting Group

2'-O-(1,1-Dioxo-thiomorpholine-4-carbothioate)-5'-O-DMTr-1'-[6-acetamido-5-nitro-2-(4-nitrophenethoxy)-pyridone]-3'-[(2-cyanoethyl)-(N,N-diisopropyl)]-phosphoramidite was used to synthesize RNA oligonucleotides on a solid support using an ABI 394 synthesizer. An RNA test sequence of 21 nucleotides containing 5 G residues, 4 C residues, 7 U residues, 4 A residues, and a single rZ nucleotide at position 10 was made using the standard TC RNA synthesis cycle and the G, C, U, A "TC" amidites purchased from Sigma-Aldrich. Removal of the NPE protecting group was necessary to prevent formation of the substitution product shown below.

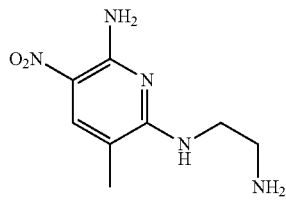

Figure 2:
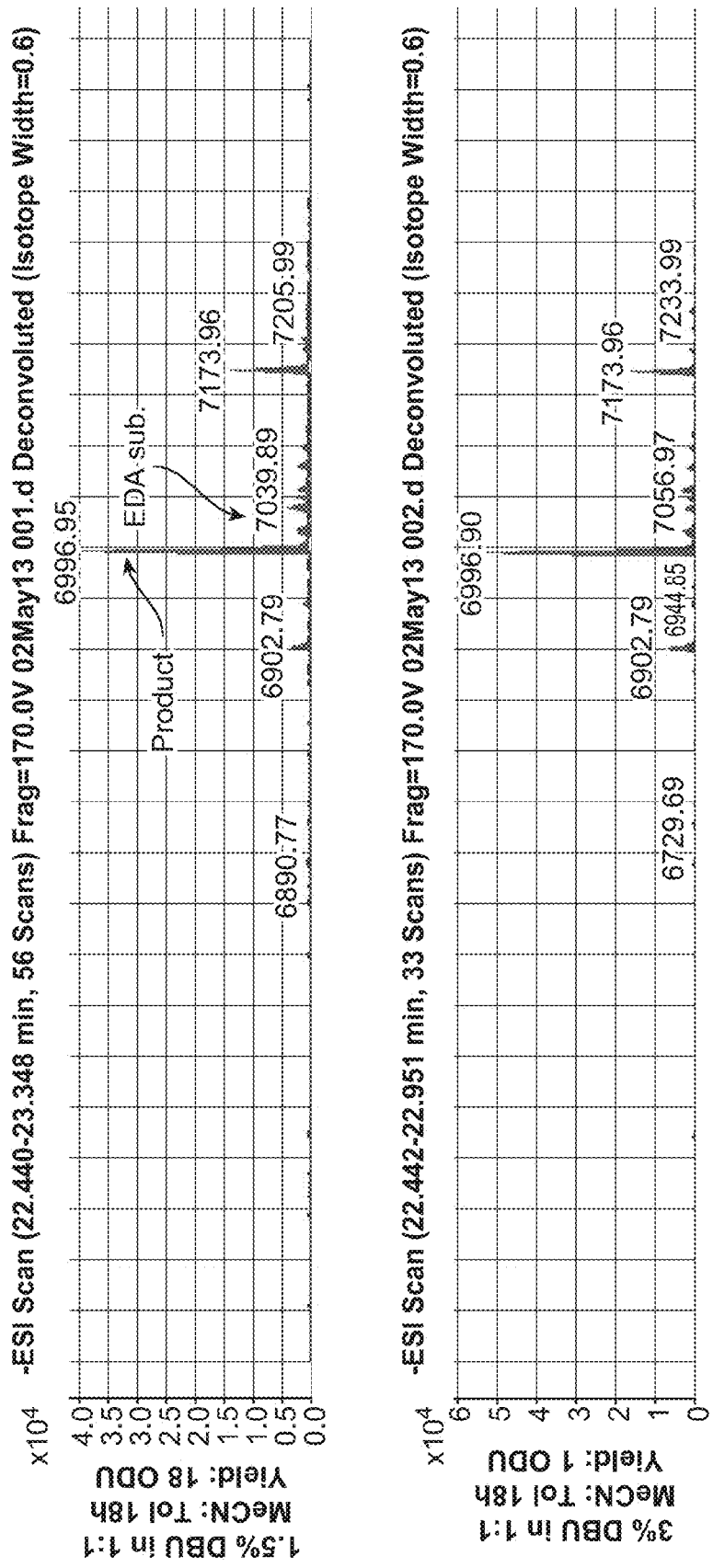
FIG. 2: Electrospray mass spectrometry plots (ESI scans) showing RNA synthesis results using para-nitrophenylethyl (NPE) as rZ protecting group and different concentrations of DBU followed by EDA for deprotection and cleavage from the support. First panel: 1.5% BDU, 18 hours; Second panel: 3% BDU, 18 hours; Third panel: 6% BDU, 18 hours; Fourth panel: 12% BDU, 18 hours. Yield is indicated at the left of each panel. EDA substituted peak is indicated as "EDA sub".
Figure 2:
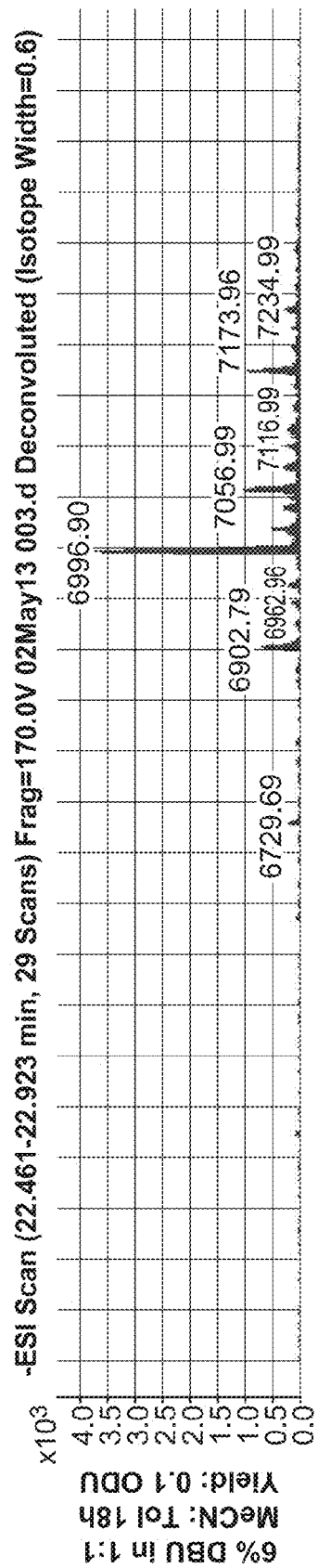
Figure 2:
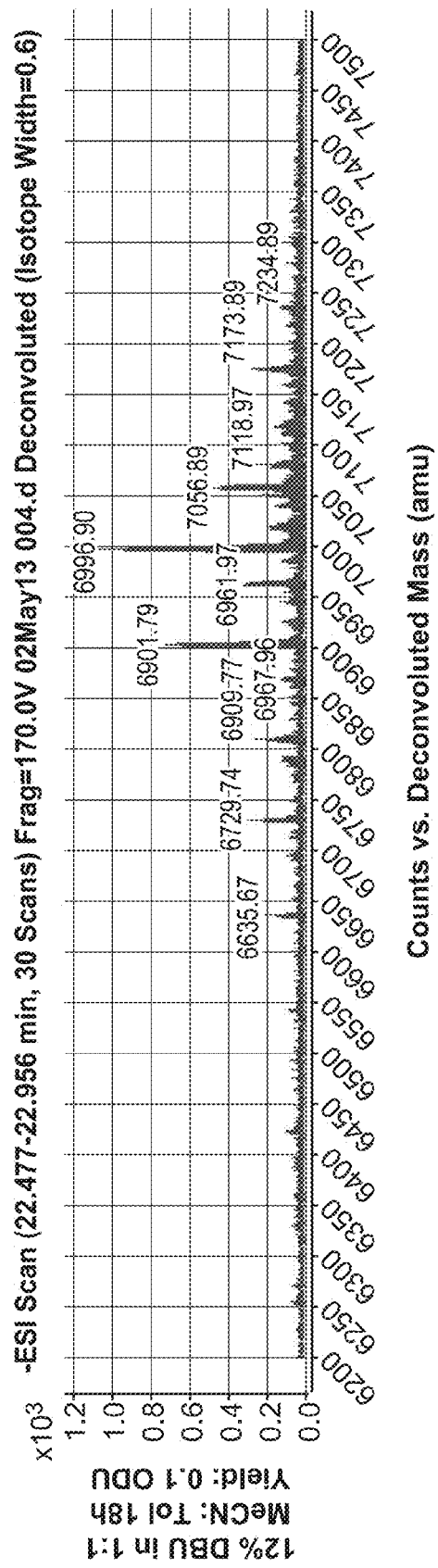

As shown in FIG. 1, top panel, this substitution product, shown as the peak at 7038.04 labeled EDA sub. (i.e., approximately 42 mass units larger than the desired product peak), was the major RNA product when only the standard, 5 hour EDA deprotection was used. A two-step protocol (1M (15%) DBU followed by EDA to complete deprotection and cleavage from the solid support) was then attempted to completely deprotect the oligonucleotide. As shown in FIG. 2, lower two panels, this protocol prevented substitution product from being formed (the EDA sub. peak was not present), but caused rapid degradation of the RNA, as evidenced by the significant peaks at the expected RNA molecular weight minus a nucleotide (which is the expected size of the RNA product lacking a G nucleotide) and −94 (which is 94 mass units smaller than the expected product). Lower amounts of DBU were tested (1.5%, 3%, 6% and 12%), but a concentration and exposure time that fully deprotected the NPE group without damaging the RNA could not be found. Further, DBU caused cleavage of the RNA from the solid support and solubilized the partially protected oligonucleotide causing a dramatic drop in yield. As shown in FIG. 2, 1.5% DBU treatment for 18 hours had the best deprotection, but 40% of the product was lost in the wash and EDA substitution was still present.

Figure 3:
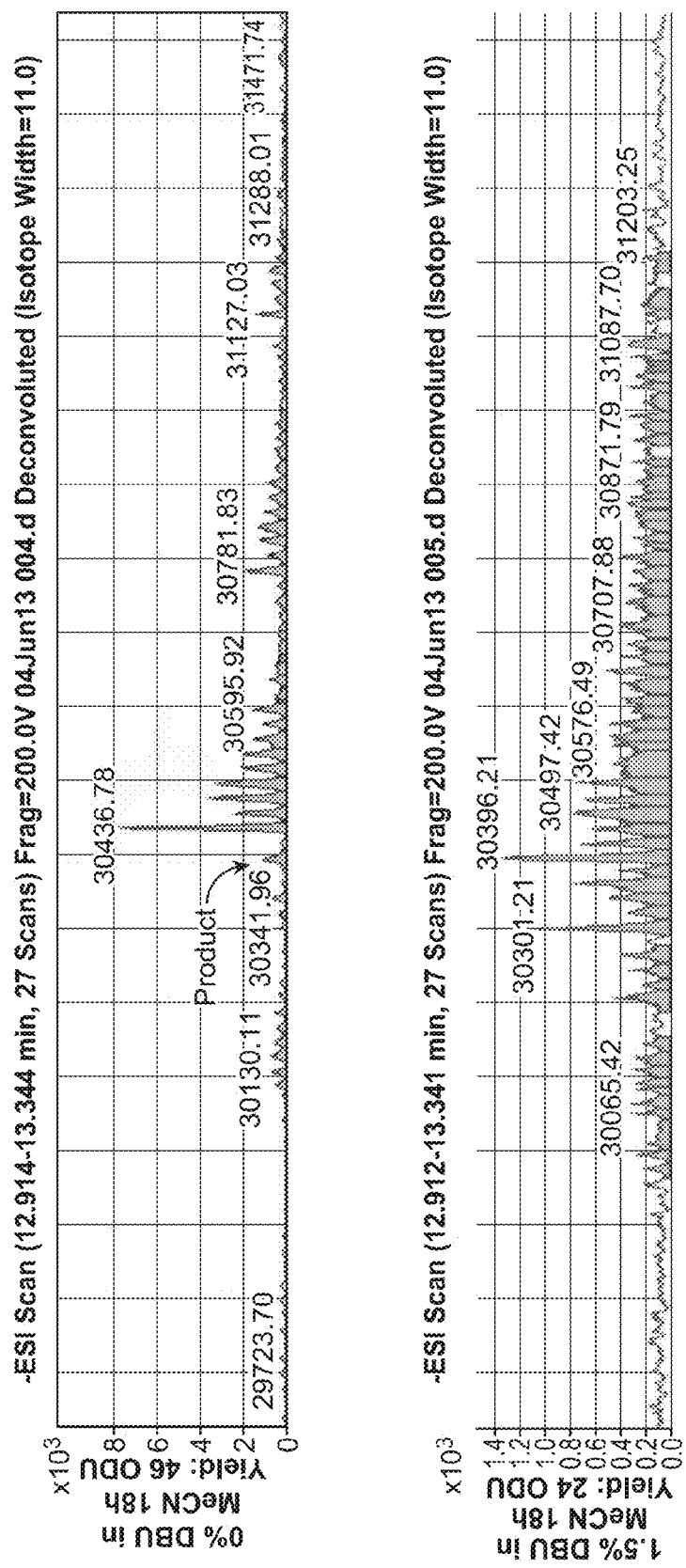
FIG. 3: Electrospray mass spectrometry plots (ESI scans) showing results of synthesis of a 93mer RNA containing a single rZ(NPE) modification and different concentrations of DBU followed by EDA for deprotection and cleavage from the support. First panel: no DBU, 18 hours; Second panel: 1.5% DBU, 18 hours; Third panel: 0.75% DBU, 18 hours; Fourth panel: 1.5% DBU in toluene, 18 hours; Fifth panel: comparison plot showing results for standard 82mer RNA that does not contain rZ but a rP base instead using EDA only for deprotection and cleavage. Product peak is indicated in the First panel.
Figure 3:
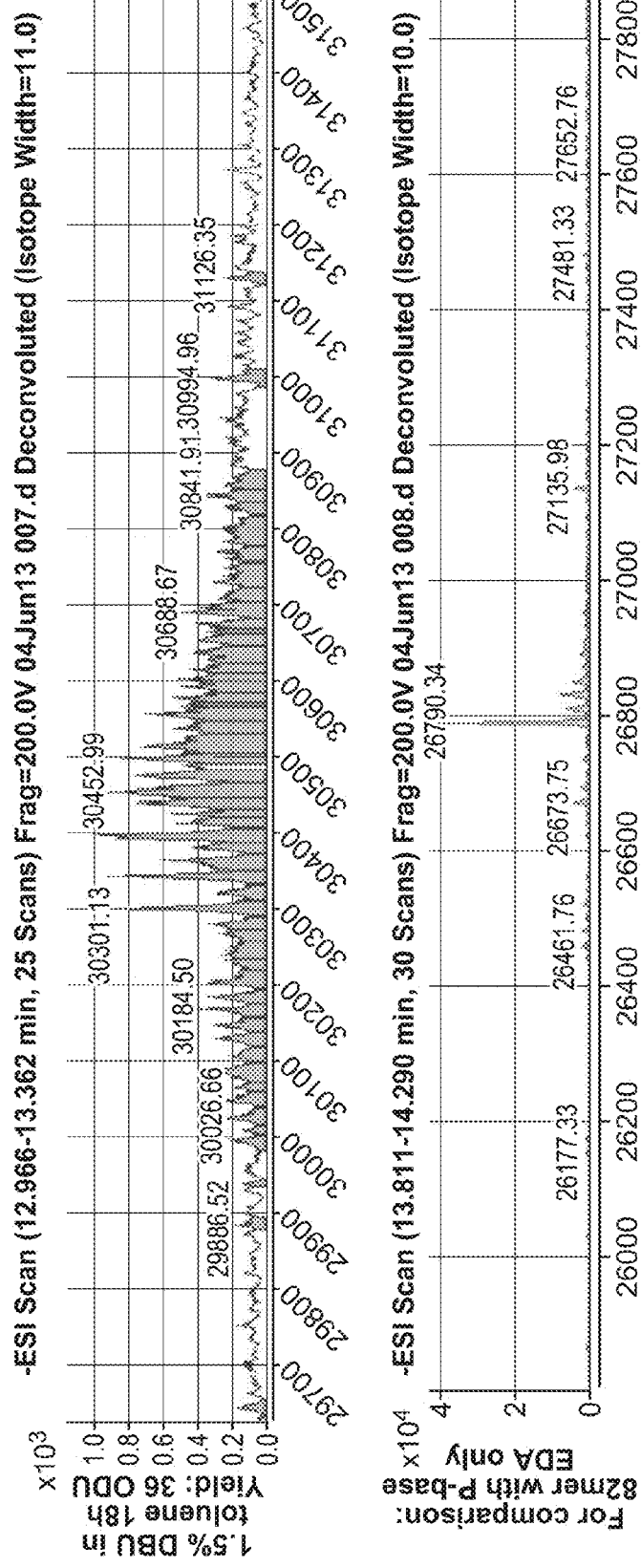

Lower DBU concentrations (0%, 0.75% and 1.5%) in MeCN were tested on an 93mer RNA containing a single rZ(NPE) modification. This caused unworkable degradation of the RNA and potential EDA substitution could not be determined (see FIG. 3, first three panels). Using toluene as the solvent with 1.5% DBU (FIG. 3, fourth panel) helped retain more RNA but a protocol for deprotection of rZ(NPE) could not be found.

Figure 4:
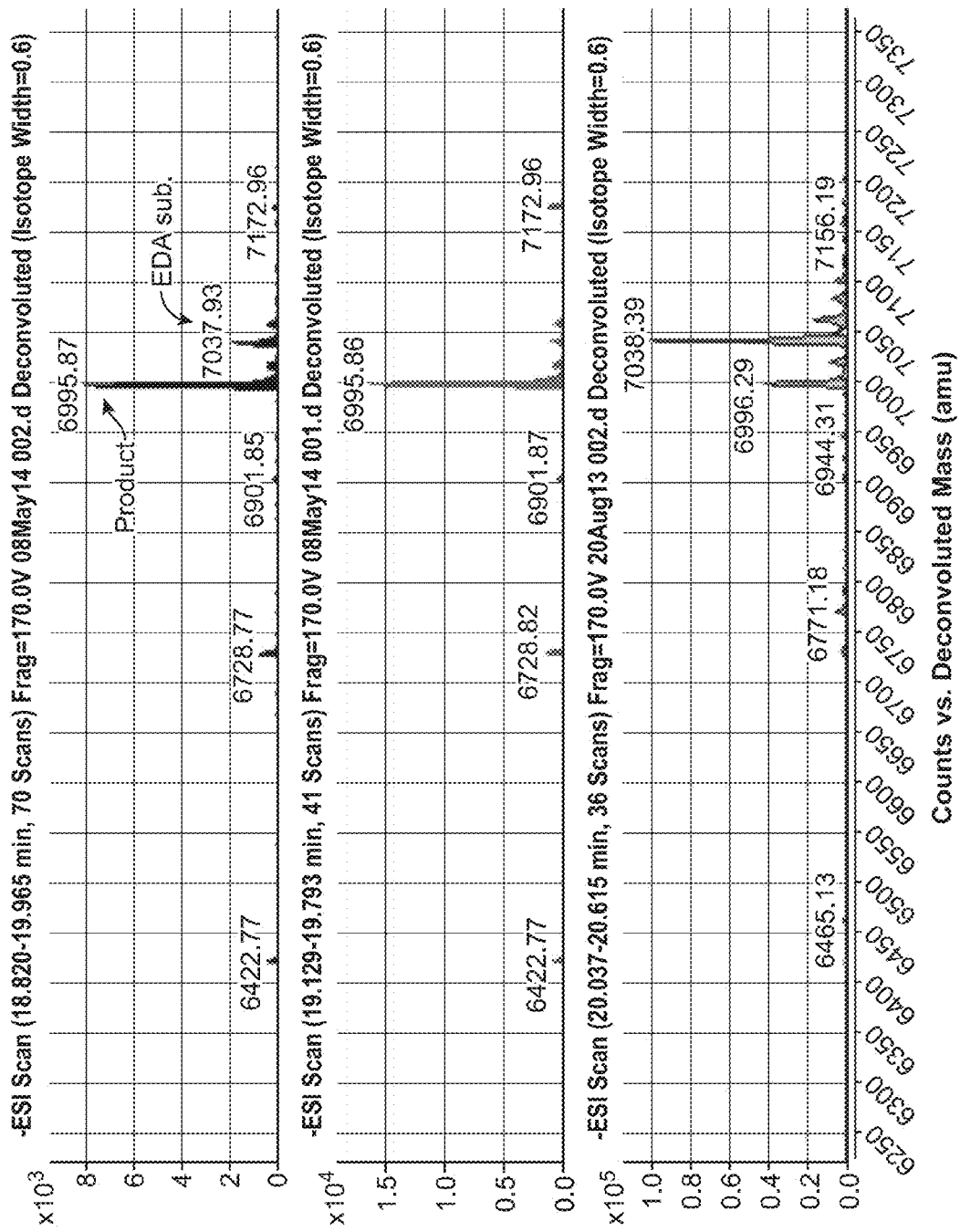
FIG. 4: Electrospray mass spectrometry plots (ESI scans) showing synthesis results of same 21mer RNA containing a single rZ nucleotide (as in FIG. 1) but protected with different carbonyloxymethyl groups. The 3 different panels correspond respectively to 5 hr EDA deprotections of ibuOM (top panel), AcOM (middle panel), and PivOM (bottom panel) of rZ containing RNA. Product peak is indicated in top panel as is the EDA substituted species (EDA sub.). PivOM protection gave the most EDA substitution, iBuOM protection allowed less, and AcOM achieved complete deprotection with no detectable substitution.

Example 3 Testing of Different Base Protecting Groups for rZ rZ amidites (compounds 6c, 6b, 6a) were synthesized respectively with isobutyryloxymethyl (iBuOM), acetyloxymethyl (AcOM), and pivaloyloxymethyl (PivOM) protecting groups in place of NPE and used to synthesize the 21 nucleotide RNA test sequence having a single rZ nucleotide at position 10 (described above). Shown in FIG. 4 are 5 hr EDA deprotections of iBuOM (top panel), AcOM (middle panel), and PivOM (bottom panel) containing 21mer RNAs. The location of the product and the EDA substituted product (EDA sub.) are indicated in the top panel. PivOM protection gave the most EDA substitution, iBuOM protection allowed less, and AcOM achieved complete deprotection with no detectable substitution.

Figure 5:
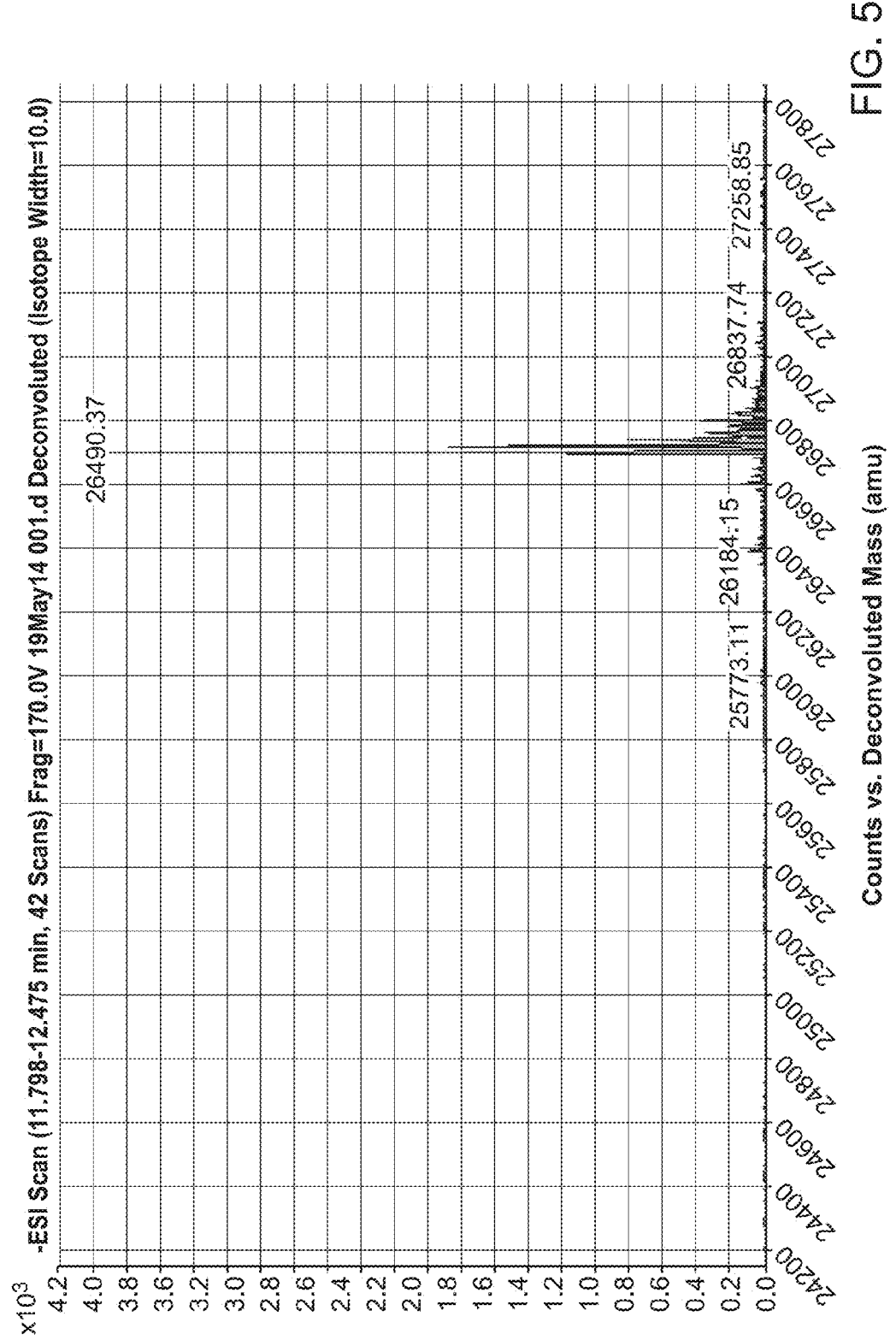
FIG. 5: Electrospray mass spectrometry plot (ESI scan) showing oligonucleotide synthesis results of a 93mer RNA containing one rZ amidite (6b) protected with acetyloxymethyl (AcOM) and 2'-O-thiocarbamate like the other TC RNA amidites after 5 hour deprotection in EDA.

Example 4 Synthesis of Oligonucleotide Using Acetyloxymethyl (AcOM) as the Protecting Group for the rZ Nucleotide A 93mer RNA containing 32 G residues, 27 C residues, 15 U residues, 18 A residues, and one AcOM protected rZ base (compound 6b) at position 36 was synthesized. "TC RNA Phosphoramidites" G, C, U and A were purchased from Sigma-Aldrich. Synthesis and deprotection protocols used were the same as described in Dellinger et al., J. Am. Chem. Soc. (2011), 133, p 11540. The rZ amidite coupled like the other TC RNA amidites. As shown in FIG. 5, the expected oligonucleotide yield was achieved after 5 hour deprotection in EDA (see product peak at 26490.37). The backside peaks are sodium and triethylamine adducts of the product. No detectable EDA substitution was observed.

Calculated mass=26491.2 Observed mass=26490.37

INCORPORATION BY REFERENCE

References and citations to other documents, such as patents, patent applications, patent publications, journals, books, papers, web contents, have been made in this disclosure. All such documents are hereby incorporated by reference herein in their entirety for all purposes. Any material, or portion thereof, that is said to be hereby incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

What is claimed is:

1. A compound having the structural formula (I):

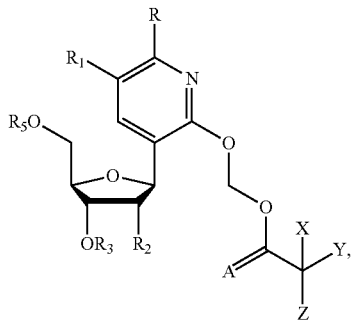

wherein
$R_1$ is $NO_2$, CN, F or $C_1$-$C_4$ perfluoroalkyl;
A is O or S;
$R_2$ is a H, halogen, O-methyl or $OR_{2'}$, wherein $R_{2'}$ is a first protecting group;
$R_3$ is a second protecting group or a phosphoramidite group;
$R_5$ is a third protecting group;
R is a protected amino group of the formula N=C(R')NR'$_2$ or N(R')COR' or N(COR')$_2$, wherein each R' is independently selected from H, linear-, branched-, saturated- or unsaturated-alkyl, aryl, alkaryl and aralkyl; or wherein R is a protected amino group of the formula N=C(R')NR'$_2$, wherein NR'$_2$ is joined to form a 5-8 membered ring wherein said ring can contain a heteroatom selected from O or S; and
each of X, Y and Z is independently H, halogen, or a $C_1$-$C_3$ alkyl, wherein two or more of X, Y and Z may together form a 5-8 membered saturated, un-saturated or aryl ring.

2. The compound of claim 1, wherein $R_{2'}$ is 1,1-dioxo-thiomorpholine-4-carbothioate (TC).

3. The compound of claim 2, wherein $R_3$ is (β-cyanoethyl)-N,N-diisopropyl phosphoramidityl, and $R_5$ is DMT.

4. The compound of claim 1, wherein $R_2$ is $OR_{2'}$, and wherein $R_{2'}$ is tert-butyldimethylsilyl (TBDMS), tri-iso-propylsilyloxymethyl (TOM), bis(2-acetoxyethoxy)methyl (ACE), pivaloyloxymethyl (PivOM), 1-(2-cyanoethoxy)ethyl (GEE), 2-cyanoethoxymethyl (CEM), —CO—R", CH$_2$—CH=CH$_2$, CH$_2$—O—CH$_2$-phenyl-NO$_2$, CH$_2$—O—CH$_2$—CH$_2$—SO$_2$-aryl, or Si(R")$_3$; wherein R" is independently selected from straight-, branched-, saturated or unsaturated-alkyl, aryl, alkaryl, and aralkyl.

5. The compound of claim 1, wherein $R_3$ is (β-cyanoethyl)-N,N-diisopropyl phosphoramidityl or methyl-N,N-diisopropylphosphoramidityl or (β-cyanoethyl)-N-pyrrolidino phosphoramidityl.

6. The compound of claim 1, wherein $R_5$ is 4,4'-dimethoxytrityl (DMT), monomethoxytrityl (MMT), trimethoxytrityl (TMT), or 9-phenylxanthyl (Px).

7. The compound of claim 1, wherein:
(a) R' is methyl, $R_1$ is $NO_2$, $R_2$ is $OR_{2'}$ and $R_{2'}$ is 1,1-dioxo-thiomorpholine-4-carbothioate (TC), $R_3$ is (β-cyanoethyl)-N,N-diisopropyl phosphoramidityl, $R_5$ is DMT, A is O, and each of X, Y, and Z is H;
(b) R' is methyl, $R_1$ is CN, $R_2$ is $OR_{2'}$, and $R_{2'}$ is 1,1-dioxo-thiomorpholine-4-carbothioate (TC), $R_3$ is (β-cyanoethyl)-N,N-diisopropyl phosphoramidityl, $R_5$ is DMT, A is O, and each of X, Y, and Z is H;
(c) R' is methyl, $R_1$ is $NO_2$, $R_2$ is $OR_{2'}$, and $R_{2'}$ is 1,1-dioxo-thiomorpholine-4-carbothioate (TC), $R_3$ is (β-cyanoethyl)-N,N-diisopropyl phosphoramidityl, $R_5$ is DMT, A is O, each of X and Y is methyl, and Z is H; or
(d) R' is methyl, $R_1$ is CN, $R_2$ is $OR_{2'}$, and $R_{2'}$ is 1,1-dioxo-thiomorpholine-4-carbothioate (TC), $R_3$ is (β-cyanoethyl)-N,N-diisopropyl phosphoramidityl, $R_5$ is DMT, A is O, each of X and Y is methyl, and Z is H.

8. An oligonucleotide, wherein at least one of the nucleotides has the structural formula of:

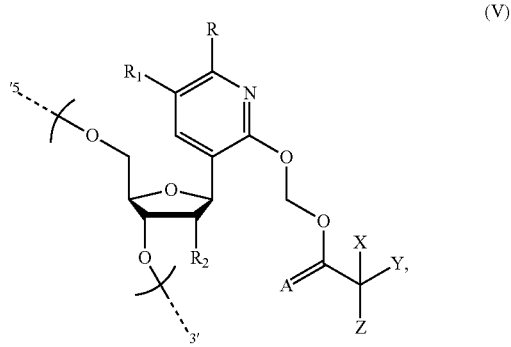

wherein
$R_1$ is an electron withdrawing group;
A is O or S;
$R_2$ is $OR_{2'}$ and $R_{2'}$ is 1,1-dioxo-thiomorpholine-4-carbothioate (TC), tert-butyldimethylsilyl (TBDMS), tri-iso-propylsilyloxymethyl (TOM), bis(2-acetoxyethoxy)methyl (ACE), pivaloyloxymethyl (PivOM), 1-(2-cyanoethoxy)ethyl (CEE), 2-cyanoethoxymethyl (CEM), —CO—R", —CH$_2$—CH=CH$_2$, —CH$_2$—O—CH$_2$-phenyl-NO$_2$, —CH$_2$—O—CH$_2$—CH$_2$—SO$_2$-aryl, or —Si(R")$_3$, wherein R" is independently selected from straight-, branched-, saturated or unsaturated-alkyl, aryl, alkaryl, and aralkyl;
R is a protected amino group of the formula N=C(R')NR'$_2$ or N(R')COR' or N(COR')$_2$, wherein each R' is independently selected from H, linear-, branched-, saturated- or unsaturated-alkyl, aryl, alkaryl and aralkyl; or wherein R is a protected amino group of the formula N=C(R')NR'$_2$, wherein NR'$_2$ is joined to form a 5-8 membered ring wherein said ring can contain a heteroatom selected from O or S; and
each of X, Y and Z is independently H, halogen, or a $C_1$-$C_3$ alkyl, wherein two or more of X, Y and Z may together form a 5-8 membered saturated, un-saturated or aryl ring.

9. The oligonucleotide of claim 8, wherein $R_2$ is $OR_{2'}$ and $R_{2'}$ is selected from: 1,1-dioxo-thiomorpholine-4-carbothioate (TC) and pivaloyloxymethyl (PivOM).

10. The oligonucleotide of claim 8, wherein $R_1$ is $NO_2$, R' is $CH_3$, A is O and each of X, Y, and Z is H.

11. The oligonucleotide of claim 8, wherein $R_2$ is $OR_{2'}$ and $R_{2'}$ is 1,1-dioxo-thiomorpholine-4-carbothioate (TC).

12. A method for synthesizing an oligonucleotide, comprising:
protecting an unnatural nucleotide with an acetyl-oxymethyl group, incorporating the protected unnatural nucleotide into a nucleotide sequence on a solid support; and removing the acetyl-oxy-methyl group from the unnatural nucleotide incorporated into the nucleotide sequence, wherein the protected unnatural nucleotide has the structural formula (V),

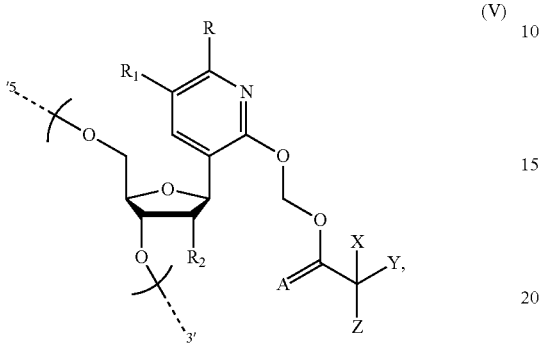

(V)

wherein
- $R_1$ is an electron withdrawing group;
- A is O or S;
- $R_2$ is $OR_{2'}$ and $R_{2'}$ is 1,1-dioxo-thiomorpholine-4-carbothioate (TC), tert-butyldimethylsilyl (TBDMS), tri-isopropylsilyloxymethyl (TOM), bis(2-acetoxyethoxy)methyl (ACE), pivaloyloxymethyl (PivOM), 1-(2-cyanoethoxy)ethyl (CEE), 2-cyanoethoxymethyl (CEM), —CO—R", —CH$_2$—CH=CH$_2$, —CH$_2$—O—CH$_2$-phenyl-NO$_2$, —CH$_2$—O—CH$_2$—CH$_2$—SO$_2$-aryl, or —Si(R")$_3$, wherein R" is independently selected from straight-, branched-, saturated or unsaturated-alkyl, aryl, alkaryl, and aralkyl; and
- R is a protected amino group of the formula N=C(R')NR'$_2$ or N(R')COR' or N(COR')$_2$, wherein each R' is independently selected from H, linear-, branched-, saturated- or unsaturated-alkyl, aryl, alkaryl and aralkyl, or wherein R is a protected amino group of the formula N=CR'NR'$_2$, NR'$_2$ is joined to form a 5-8 membered ring wherein said ring can contain a heteroatom selected from O or S;
- each of X, Y and Z is independently H, halogen, or a $C_1$-$C_3$ alkyl, wherein two or more of X, Y and Z may together form a 5-8 membered saturated, un-saturated or aryl ring.

13. The method of claim 12, wherein $R_2$ is $OR_{2'}$ and $R_{2'}$ is 1,1-dioxo-thiomorpholine-4-carbothioate (TC).

14. The method of claim 12, wherein $R_2$ is $OR_{2'}$ and $R_{2'}$ is pivaloyloxymethyl (PivOM).

15. The method of claim 12, wherein $R_1$ is NO$_2$, R' is CH$_3$, A is O and each of X, Y and Z is H.

16. The method of claim 15, wherein $R_2$ is $OR_{2'}$ and $R_{2'}$ is 1,1-dioxo-thiomorpholine-4-carbothioate (TC).

17. The method of claim 12, wherein removing the acetyl-oxy-methyl group is accomplished with a one-step reaction with a base.

18. The method of claim 17, wherein the base is ethylenediamine or ammonia.

19. The method of claim 17, wherein $R_2$ is O-TC, H, F or O-methyl and wherein the method further comprises contacting the oligonucleotide with is a reagent comprising ethylenediamine to deprotect the oligonucleotide and cleave the oligonucleotide from the solid support in a single step.

20. The method of claim 17, wherein $R_2$ is O-pivaloyloxymethyl (O-PivOM), H, F or O-methyl and wherein the method further comprises contacting the oligonucleotide with a reagent comprising ammonia to deprotect the oligonucleotide and cleave the oligonucleotide from the solid support in a single step.

* * * * *

UNITED STATES PATENT AND TRADEMARK OFFICE
CERTIFICATE OF CORRECTION

PATENT NO. : 9,802,975 B2
APPLICATION NO. : 14/724613
DATED : October 31, 2017
INVENTOR(S) : Benjamin D. Lunstad et al.

It is certified that error appears in the above-identified patent and that said Letters Patent is hereby corrected as shown below:

On the Title Page

In item (56), in Column 2, under "Other Publications", Line 4, delete "Nutter," and insert -- Hutter, --, therefor.

In the Specification

In Column 8, Line 17, delete "pyrrolodinoamidine," and insert -- pyrrolidinopyridine, --, therefor.

In Column 8, Line 37, delete "queosine," and insert -- queuosine, --, therefor.

In Column 26, Lines 50-51, delete "(pivaloyloxmethyl)" and insert -- (pivaloyloxymethyl) --, therefor.

In Column 26, Line 67, after "TIPDS)" insert -- . --.

In Column 27, Lines 3-4, delete "(pivaloyloxmethyl)" and insert -- (pivaloyloxymethyl) --, therefor.

In Column 27, Lines 20-21, delete "(pivaloyloxmethyl)" and insert -- (pivaloyloxymethyl) --, therefor.

In Column 27, Line 33, delete "(pivaloyloxmethyl)" and insert -- (pivaloyloxymethyl) --, therefor.

In Column 27, Line 47, delete "(pivaloyloxmethyl)" and insert -- (pivaloyloxymethyl) --, therefor.

In Column 28, Lines 6-7, delete "(acetyloxymethyl)" and insert -- (acetoxymethyl) --, therefor.

In Column 28, Lines 26-27, delete "(acetyloxymethyl)" and insert -- (acetoxymethyl) --, therefor.

In Column 28, Lines 43-44, delete "(acetyloxymethyl)" and insert -- (acetoxymethyl) --, therefor.

In Column 28, Line 56, delete "(acetyloxymethyl)" and insert -- (acetoxymethyl) --, therefor.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,802,975 B2

In Column 29, Line 6, delete "(acetyloxymethyl)" and insert -- (acetoxymethyl) --, therefor.

In Column 31, Lines 2-3, delete "(benzoyloxmethyl)" and insert -- (benzyloxymethyl) --, therefor.

In the Claims

In Column 33, Line 49, in Claim 4, delete "(GEE)," and insert -- (CEE), --, therefor.

In Column 34, Line 3, in Claim 7, delete "$OR_{2'}$," and insert -- $OR_{2'}$ --, therefor.

In Column 34, Line 8, in Claim 7, delete "$R_t$" and insert -- $R_1$ --, therefor.

In Column 34, Line 67, in Claim 12, delete "group," and insert -- group; --, therefor.

In Column 36, Line 27, in Claim 19, after "with" delete "is".